(12) United States Patent
Whayne et al.

(10) Patent No.: US 11,331,139 B2
(45) Date of Patent: May 17, 2022

(54) METHODS TO PREVENT STRESS REMODELING OF ATRIAL TISSUE

(71) Applicant: AtriCure, Inc., Mason, OH (US)

(72) Inventors: James G. Whayne, Cary, NC (US); Sidney D. Fleischman, Durham, NC (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 16/157,902

(22) Filed: Oct. 11, 2018

(65) Prior Publication Data
US 2019/0090945 A1 Mar. 28, 2019

Related U.S. Application Data

(63) Continuation of application No. 14/605,790, filed on Jan. 26, 2015, now Pat. No. 10,123,836.
(60) Provisional application No. 61/931,469, filed on Jan. 24, 2014.

(51) Int. Cl.
| | | |
|---|---|---|
| *A61B 18/14* | (2006.01) | |
| *A61B 18/00* | (2006.01) | |
| *A61B 18/24* | (2006.01) | |
| *A61B 90/30* | (2016.01) | |

(52) U.S. Cl.
CPC .......... *A61B 18/1492* (2013.01); *A61B 18/24* (2013.01); *A61B 90/30* (2016.02); *A61B 2018/00357* (2013.01); *A61B 2018/00577* (2013.01); *A61B 2018/00839* (2013.01); *A61B 2018/00982* (2013.01)

(58) Field of Classification Search
CPC ............... A61B 18/1492; A61B 18/24; A61B 2018/00357; A61B 2018/00577; A61B 2018/00839; A61B 2018/00982
See application file for complete search history.

(56) References Cited

U.S. PATENT DOCUMENTS

| 6,071,274 | A | | 6/2000 | Thompson et al. | |
|---|---|---|---|---|---|
| 6,164,283 | A | * | 12/2000 | Lesh ...................... | A61B 18/10 128/898 |
| 8,204,591 | B2 | * | 6/2012 | Ben-David .......... | A61N 1/0556 607/1 |
| 9,572,624 | B2 | | 2/2017 | Ibrahim et al. | |
| 2002/0087151 | A1 | * | 7/2002 | Mody ................ | A61B 18/1492 606/15 |
| 2006/0009759 | A1 | * | 1/2006 | Chrisitian .......... | A61B 18/1492 606/41 |
| 2015/0150643 | A1 | * | 6/2015 | Trayanova ............. | A61B 34/10 606/34 |

* cited by examiner

*Primary Examiner* — Lindsey G Wehrheim
(74) *Attorney, Agent, or Firm* — Levine Bagade Han LLP

(57) ABSTRACT

Methods and devices are disclosed herein for therapeutically treating atrial tissue to lessen the effects of mechanical stress on atrial tissue, where reducing mechanical stress in the portion of atrial tissue reduces formation of at least one arrhythmia substrate. In one example, the devices and methods are suitable for minimally invasive surgery. More particularly, methods and devices described herein permit creating an ablation pattern on an organ while reducing excessive trauma to a patient.

14 Claims, 15 Drawing Sheets

METHODS TO PREVENT STRESS REMODELING OF ATRIAL TISSUE

RELATED APPLICATIONS

This application is a continuation of U.S. patent application Ser. No. 14/605,790 filed Jan. 26, 2015, which is a non-provisional of U.S. Provisional Application No. 61/931,469 filed Jan. 24, 2014, the contents of which are incorporated herein by reference in its entirety.

BACKGROUND OF THE INVENTION

Field of the Inventions

Methods and devices are disclosed herein for therapeutically treating atrial tissue to lessen the effects of mechanical stress on atrial tissue, where reducing mechanical stress in the portion of atrial tissue reduces formation of at least one arrhythmia substrate. In one example, the devices and methods are suitable for minimally invasive surgery. More particularly, methods and devices described herein permit creating an ablation pattern on an organ while reducing excessive trauma to a patient.

Description of the Related Art

Atrial fibrillation surgery requires creation of an ablation or coagulation lesion in atrial tissue. Typically, a physician creates a lesion using energy (including but not limited to radiofrequency, D.C., microwave, cryo, laser or other thermal modalities) to prevent wavelets or electrical signals/impulses that propagate through the cardiac tissue to sustain atrial fibrillation or produce atrial flutter, atrial tachycardia, or other arrhythmia.

Many conventional approaches in applying energy to the cardiac tissue face difficulties in attempting to create a complete lesion pattern that prevents propagation of the electrical impulse across the lesion pattern. Some factors attributable to these difficulties are tissue contact throughout the length of the electrode(s) is/are not consistent causing variability in the transmission of energy throughout the target length of ablated/coagulated tissue. Moreover, surrounding anatomic features also contributes to the difficulty in creating a complete lesion pattern. As a result, an incomplete lesion or lesion pattern includes one or more gaps of viable or semi-viable tissue that allows propagation of wavelets through tissue and through the lesion pattern.

Another factor in the inability of existing thermal ablation systems to create complete curvilinear, transmural lesions is the presence of convective cooling on the opposite surface of the atrium. This convective cooling produces a heat sink that decreases the maximum temperature at this surface thereby preventing the lesions from consistently extending transmurally through the entire wall of the atrium. This is especially relevant during beating-heart procedures in which the coagulation/ablation probe is placed against the epicardial surface, and blood flowing along the endocardium removes heat thus producing a larger gradient between temperature immediately under the electrodes along the epicardium and that the temperature at the endocardium.

Apart from improving treatment of existing cases of atrial fibrillation, there are not many options relating to preventative measures to address the causation of atrial fibrillation. The mechanisms leading to the development of persistent atrial fibrillation are not well known. In addition, the connection between various ablation procedures and long-term outcomes has not been established, in many cases the effectiveness of endocardial ablation outcomes decline over time and often require multiple repeat ablation procedures. Identifying the progression of atrial remodeling that produces persistent AF, treatments and performing treatments to address the effects of this remodeling can provide treatments that are designed to counteract the underlying causes to not only interrupt current atrial fibrillation substrates but also prevent future atrial fibrillation substrates from developing. Treatments based on such remodeling can also help identify target ablation locations to complement pulmonary vein isolation in patients with structural heart disease, enlarged atria, high Body Mass Index (BMI), and/or longstanding complex forms of AF.

Most research and treatments focus on endocardial pulmonary vein isolation (PVI) approaches and ignore the importance of the attachments between the atria and pericardium (e.g. pericardial reflections). In addition, most treatments avoid ablation along the posterior left atrium due to the proximity of the esophagus. These limitations hinder the ability to target anatomic substrates caused by atrial stretch due to mechanical stresses, especially those emanating from the pericardial reflections along the posterior left atrium. The impact of these mechanical stresses to the development and progression of persistent AF is substantial. Understanding stress-induced remodeling and its role in AF progression defines a treatment that addresses current substrates initiating and/or maintaining AF, and reduces the stresses preventing continued remodeling and new substrate development.

Atrial stretch, the enlargement, progression and/or displacement of the atrial tissue due to underlying medical conditions is believed to cause calcium overload, calcineurin activation, and changes in metalloproteinases (MMPs) and Tissue inhibitors of metalloproteinases (TIMPs). In addition, the AT1 receptor appears to be involved. Weerasooriya R, et al. *Catheter ablation for atrial fibrillation: are results maintained at 5 years of follow-up?* J Am Coll Cardiol. 2011; 57:160-6. Atrial stretch also seems to result in inflammation. In preclinical animal models, atrial stretch inducing increased atrial fibrosis causes regional conduction slowing, which may increase the likelihood to develop AF. It is believed that stretch of the atria is a main contributor to atrial remodeling.

In addition, Mitral Valve regurgitation increases pressure in the left atrium and clipping the left atrial appendage may increase pressure in the left atrium leading to atrial stretch and eventually atrial fibrillation. Moreover, use of left atrial appendage occlusion devices often causes the atrium to expand more rapidly causing more atrial stretch which leads to more atrial fibrilation.

Atrial remodeling comprises atrial structural changes. Such changes have been observed in animal models of AF with or without underlying diseases and include (i) atrial enlargement, (ii) cellular hypertrophy, (iii) dedifferentiation, (iv) fibrosis, (v) apoptosis, and (vi) loss of contractile apparatus (myolysis), and changes in size and shape of the mitochondria, disruption of the sarcoplasmatic reticulum, and homogeneous distribution of nuclear heterochromatin. It is believed that atrial structural remodeling is the main contributor for initiation and persistence of atrial fibrillation.

Electrical remodeling, meaning the ability of the tissue to conduct an electrical signal or current, is caused by changes in ionic properties of cardiomyocytes (shortening refractoriness and slowing conduction velocity) due to high atrial rates. It is believed to be completely reversible if sinus rhythm can be restored. Structural remodeling is characterized by loss of cardiomyocytes, alteration in extracellular matrix, and fibrosis; can cause non-homogeneity in electrical propagation, slower conduction velocity, and electrical uncoupling.

Structural remodeling is believed to be much less reversible even when sinus rhythm is restored.

Fibrotic diseases are characterized by replacement of normal tissue with a collagen-rich matrix that can disrupt organ function. Studies show that when persistent collagen production outpaces or overwhelms mechanisms that remove collagen, excess collagen is deposited in the extracellular matrix, leading to tissue fibrosis in the tissue. Left atrium stiffness is believed to be an independent predictor of recurrent AF after ablation procedures. A LA stiffness index <65.3 mmHg observed >90% AF free probability versus <45% when the index is ≥65.3 mmHg. Studies show that atrial fibrosis increases atrial stiffness and worsens the reservoir function and is reported to be a predictor of AF recurrence after ablation procedures.

There remains a need to address current substrates which give rise to atrial fibrillation. There also remains a need to attempt to prevent the formation of new substrates that form as a result of stress induced modification of atrial tissue from underlying medical conditions, which lead to atrial fibrillation.

SUMMARY OF THE INVENTION

Aspects of the invention are directed to methods treating atrial fibrillation. The subject coagulation probes for ablation and/or coagulation integrate suction to the coagulation mechanism so as to ensure consistent and intimate tissue contact directly between the coagulation mechanism and soft tissue.

In one variation such a method includes identifying an affected region of the atrial tissue, where the affected region of the atrial tissue is subject to a mechanical stress produced as a result of an existing medical condition; producing a treated section of the atrial tissue by applying energy thereto, such that the treated section of the atrial tissue provides increased mechanical support to the affected region of the atrial tissue, where the increased mechanical support reduces the mechanical stress in the affected region of tissue to reduce the occurrence of atrial fibrillation within the atrial tissue.

The medical conditions affecting the heart can include obesity, hypertension, cardiomyopathy, or any other condition that gives rise to creating areas of stress in atrial tissue.

In certain variations, the method includes producing a plurality of parallel and adjacent lesions on a posterior left atrium surface. In some cases at least two of the plurality of parallel and adjacent lesion overlap.

The treatments can be applied to any area of the heart that would not result in further worsening of the hearts ability to function. For example, producing a treated section of the atrial tissue can include producing a plurality of lesions on an oblique sinus region of the atrium. Producing the plurality of lesions on an oblique sinus region of the atrium can include overlapping a plurality of the lesions to electrically silence the oblique sinus region.

The methods discussed herein can be also used to ablate at least one existing substrates of tissue causing atrial fibrillation.

The patterns discussed herein can include patterns created on an epicardial surface, patterns created on an endocardial surface, and/or a combination thereof.

In another example, the present disclosure includes a method of treating a heart, comprising locating a portion of an atrial tissue of the heart where the portion of atrial tissue is subject to a mechanical stress as a result of an existing medical condition; identifying a treatment area of the atrial tissue based on the portion of the atrial tissue subject to high mechanical stress; and applying energy to at least a portion of the treatment area of atrial tissue to create an treated area of atrial tissue that reduces the mechanical stress on the portion of atrial tissue, where reducing mechanical stress in the portion of atrial tissue reduces formation of at least one arrhythmia substrate.

In another variation, the method includes treating a heart where a portion of an atrial tissue of the heart is subject to a mechanical stress as a result of an existing medical condition. In one example, this method can include creating a series of lesions in the atrial tissue in a number of locations in the atrial tissue, where the series of lesions and the number of locations increase a structural support of the atrial tissue resulting in a reduction of the mechanical stress on the portion of atrial tissue, where reducing mechanical stress in the portion of atrial tissue reduces formation of at least one arrhythmia substrate.

In another variation, a method of treating atrial fibrillation can include coagulating tissue to create a bi-atrial coagulation pattern on a first and a second atrial surfaces where the first atrial surface and the second atrial surface are located on opposite sides of the cardiac tissue. For example, such a method comprises identifying at least one region of cardiac tissue subject to mechanical stress as a result of produced as a result of an adverse medical condition; positioning a first coagulation device adjacent to the first atrial surface of the cardiac tissue; creating a first coagulation pattern on the first atrial surface with the first coagulation device, where the first coagulation pattern results in a reduction of mechanical stress on a portion of the cardiac tissue; positioning a second coagulation device adjacent to the second atrial surface of the cardiac tissue; creating a second coagulation pattern on second surface with the second coagulation device, where the second coagulation pattern results in further reduction of mechanical stress on a portion of the cardiac tissue; and where reducing mechanical stress in the portion of cardiac tissue reduces formation of at least one arrhythmia substrate.

Variations of the devices, methods and procedures described herein include combinations of features of the various embodiments or combination of the embodiments themselves wherever possible.

DETAILED DESCRIPTION

Methods and devices described herein provide for creating an ablation or coagulation patterns to address regions of high stress in atrial tissue that are often caused by underlying medical conditions that adversely affect the heart and cardiac tissue such as obesity, hypertension, cardiomyopathy, etc.

The lesions can be made on an endocardial and/or on an epicardial surface. The coagulation pattern comprises any number of coagulation lesions that are contiguous such that the lesions overlap, intersect, and/or join. In one variation, the contiguous lesion forms a barrier to prevent any electrical signal from propagating through or across the lesion pattern. The techniques involved in creating a bi-atrial lesion pattern can be applied to other organs or structures of the body. Accordingly, unless specified otherwise, the methods and devices are not limited to use in cardiac structures.

The methods and devices described herein can be used with conventional approaches for accessing and positioning a coagulation device adjacent to endocardial as well as those techniques for positioning a coagulation device adjacent to epicardial tissues. However, positioning of the coagulation device in an endocardial application can also employ various techniques that allow for improved manipulation of organs and/or instruments in the thoracic cavity. These improved techniques allow for direct visualization along the posterior region of the heart and other anatomic structures not attainable with conventional thoracic approaches. In one instance, the access devices described herein can be combined with a rail-member for accurate positioning of treatment devices over tissue.

Figure 1A:
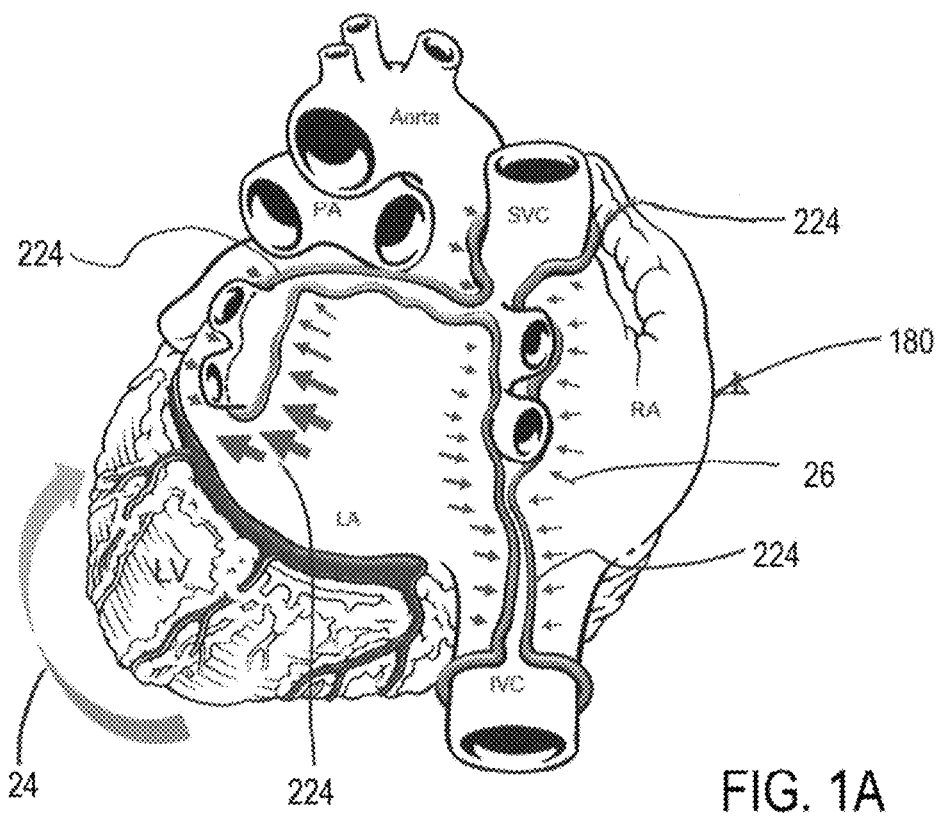
FIG. 1A illustrates the pericardial reflections tether the atria to the pericardium.

The pericardial reflections define regions of high mechanical stress causing atrial stretch and remodeling in response to underlying conditions (e.g. hypertension). The posterior left atrium, tethered to the pericardium at the reflections, are embryological extensions of the pulmonary veins making this oblique sinus region susceptible to the development of AF substrates, especially when exposed to conditions that produce atrial stretch. FIG. 1A illustrates the pericardial reflections 224 that tether the atria to the pericardium. As illustrated, these reflections 224 extend along the right heart 180 from the SVC to the right pulmonary vein ostia to the IVC. The reflections 224 cross the high posterior roof from the superior aspect of the RPV ostium to the superior aspect of the left pulmonary veins and incorporate the LPV ostium. The SVC, PV antra, posterior LA roof, and IVC are anchored to the pericardium.

Figure 1B:
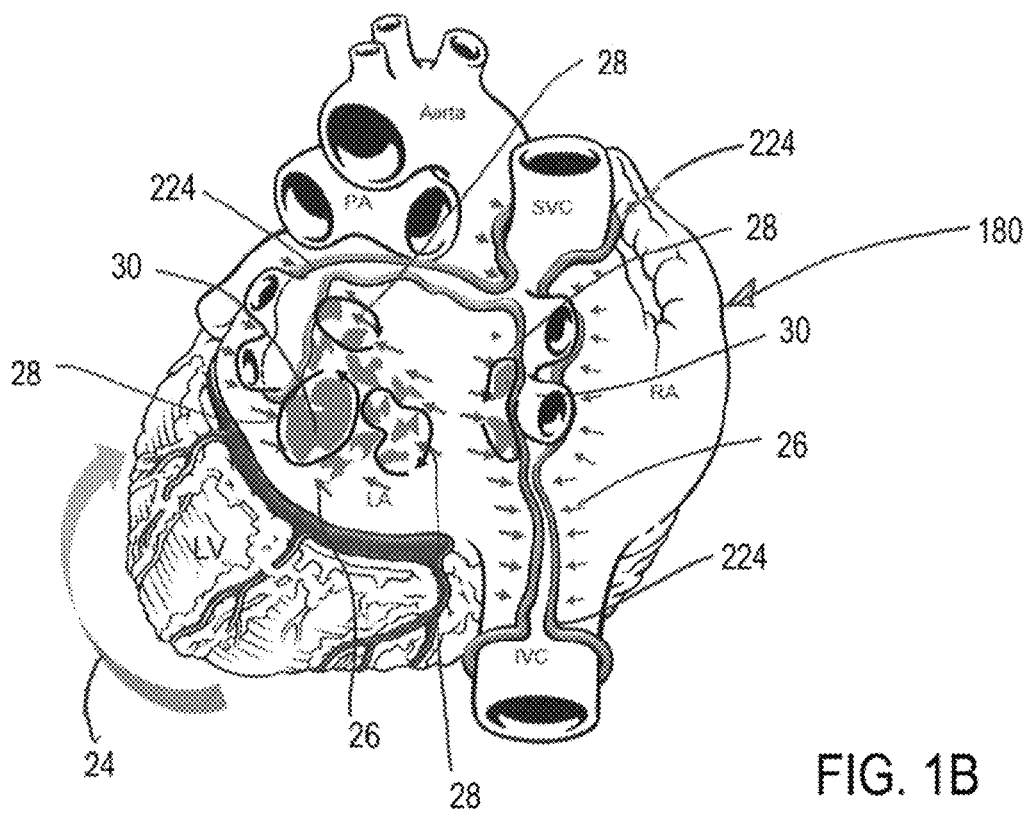
FIG. 1B illustrates a condition of the left atrium where the areas of fibrosis form as a result of the stress applied to the atrial tissue.

Displacement of the heart, as illustrated by arrow 24, produces regions of tensile stresses designated by arrows 26. Continued application of these stresses ultimately lead to atrial stretch and fibrosis in the atrial tissue. As shown, the areas of increased stress are often adjacent to the reflections 224. FIG. 1B illustrates a condition of the heart 180 where the areas of fibrosis 30 form as a result of the stress applied to the atrial tissue. These areas of fibrosis 30 can potentially give rise to arrhythmogenic wave fronts 28 responsible for atrial fibrillation.

As shown, the pulmonary veins are tethered at the pericardial reflections, which inhibit movement of the pulmonary veins. This fixation is believed to be responsible for increased stress at the location adjacent to these regions as illustrated by areas 26. The deformation 24 of the heart translates into higher stresses at the attachment points (e.g., the pericardial reflections, pulmonary veins, inferior vena cava and superior vena cava). The posterior left atrium also experiences minimal movement due to the lack of movement of the pulmonary veins, so ablating the posterior left atrium is not believed to impair atrial function. However, the anterior left atrium and left atrial appendage contribute the most to atrial ejection fraction (e.g. the measurement of blood leaving the heart during contraction) and therefore should be preserved. The venous left atrium or posterior left atrium is tether to the pericardium and is believed to contribute only minimally to atrial ejection fraction.

Figure 1C:
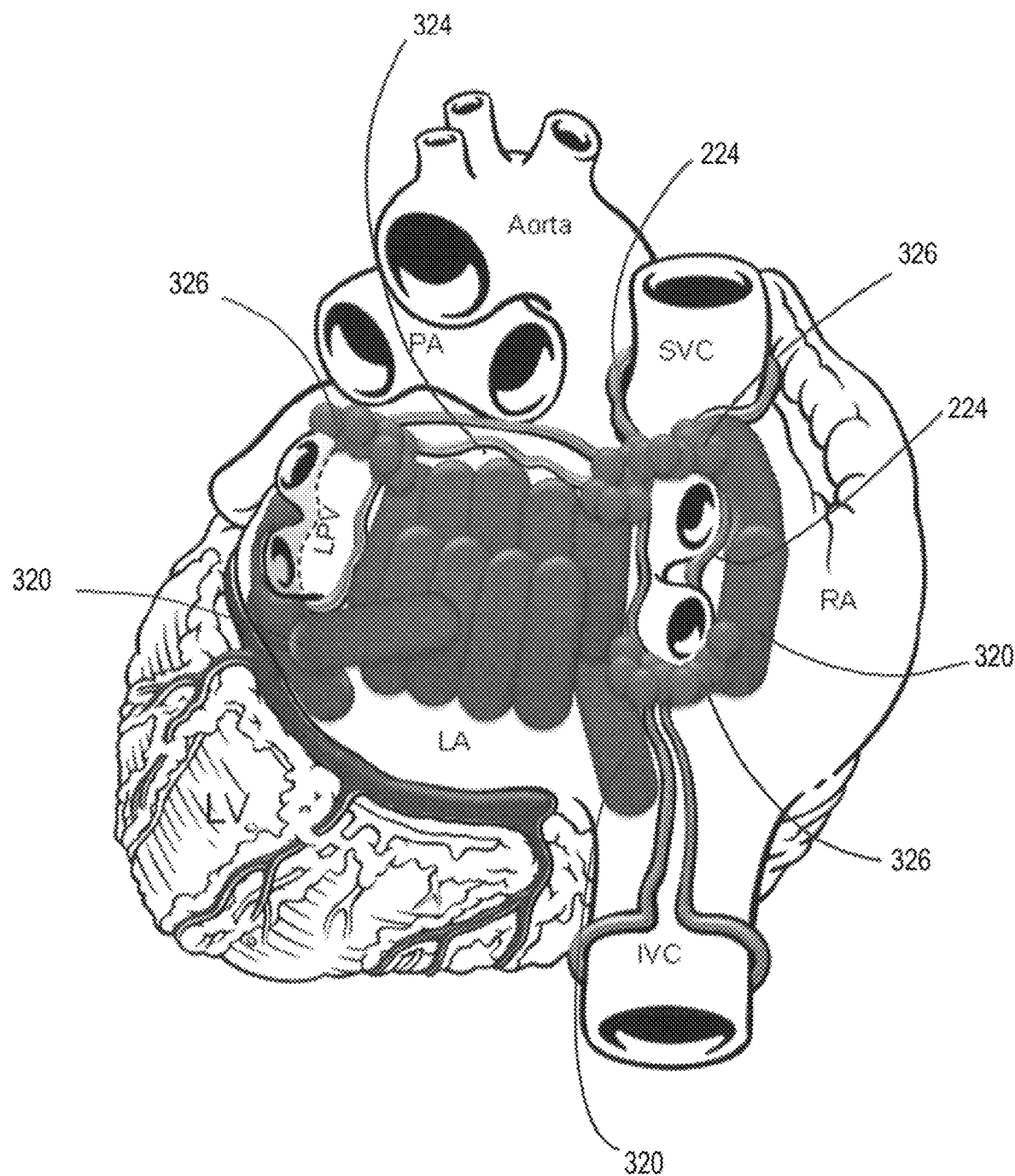
FIG. 1C shows an example of a treatment pattern that can reduce and preventing atrial fibrillation in an atrial tissue of a heart.

FIG. 1C shows an example of a treatment pattern that can reduce and preventing atrial fibrillation in an atrial tissue of a heart. In this example, the treatment pattern coagulates or ablates current substrates giving rise to atrial fibrillation and also reinforces the posterior left atrium to reduce stresses to prevent new substrates from developing. The illustrated example shows both epicardial treatment patterns 326 and endocardial patterns 320. As shown, the patterns in this variation are along the pericardial reflections 224. The treatment patterns can be created with a number of treatment devices as discussed herein. The epicardial lesions 320 are designed to reinforce the posterior left atrium tethered by the reflections 224 especially below the left inferior pulmonary vein to the right inferior pulmonary vein. This reinforcement supports the posterior left atrium when exposed to external forces such as obesity, hypertension, cardiomyopathy, etc. (as described above) in which the displacement of the heart would otherwise causes stress on the left atrium adjacent to the pericardial reflections where the largest mismatch in compliance exists. This treated area also provides increased mechanical support to help prevent high stress regions that would otherwise create atrial stretch and result in atrial remodeling that produces AF substrates.

FIG. 1C also illustrates a variation of a treatment pattern where the epicardial lesions 320 are placed adjacently so that any gaps in the lesions are blocked by adjacent lesions. Conventional treatment patterns (e.g., "box" lesion around the pulmonary veins) can leave gaps that may lessen the effectiveness of the treatment. The illustrated lesions should be sufficient to silence the posterior extensions residing within the oblique sinus and outlined by the pericardial reflections. By maintaining the lesion patterns in a relatively straight orientation, treatment devices device can be advanced completely up to the superior roof pericardial reflection 324 without distorting the device. This also allows for the physician to create and connect several adjacent lesions. The resulting overlap ensures complete electrical silence within this posterior oblique sinus region.

It is understood that any number of treatment patterns that serve to increase structural support and reduce the such that the treated section of the atrial tissue provides increased mechanical support to the affected region of the atrial tissue, where the increased mechanical support reduces the mechanical stress in the affected region of tissue to reduce the occurrence of atrial fibrillation within the atrial tissue. Additional treatment patterns can be created based upon the atrial stress distribution, which depends on the location and anatomy of the pericardial reflections specific to the patient. Measurement of the atrial stress distribution can be performed with MRI, electro-anatomic mapping (EAM), or other non-invasive imaging to determine areas of disease progression and/or regions of fibrosis along atrial tissue such as fibrosis along the posterior left atrium.

Figure 2A:
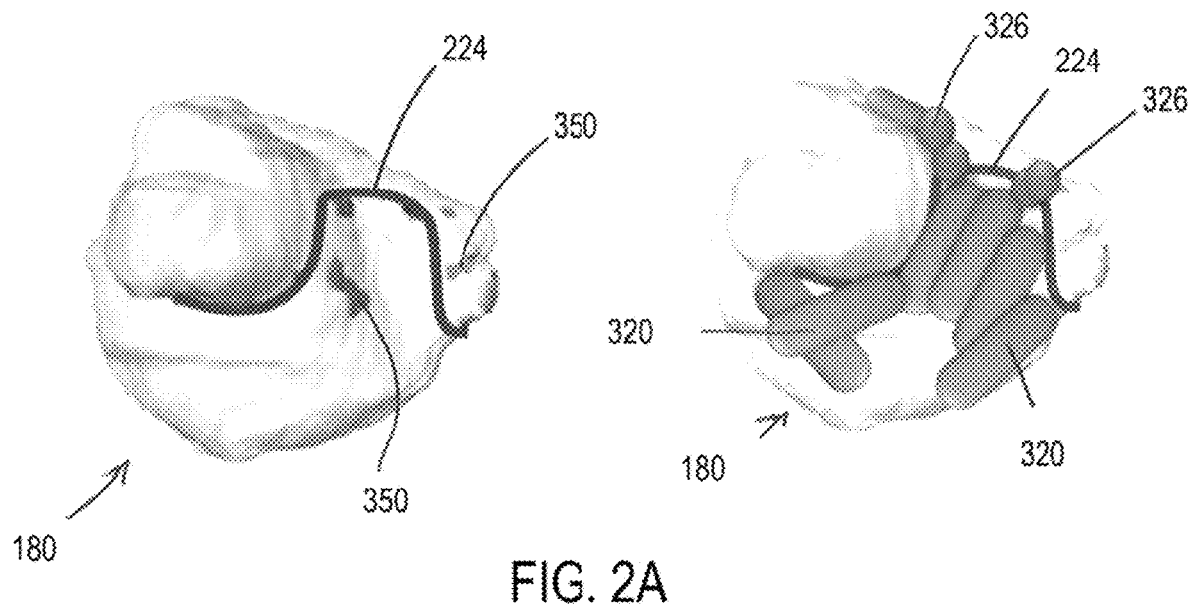
FIGS. 2A through 2D illustrate three dimensional images of hearts having varying degrees of fibrosis and accompanying lesion patterns.
Figure 2B:
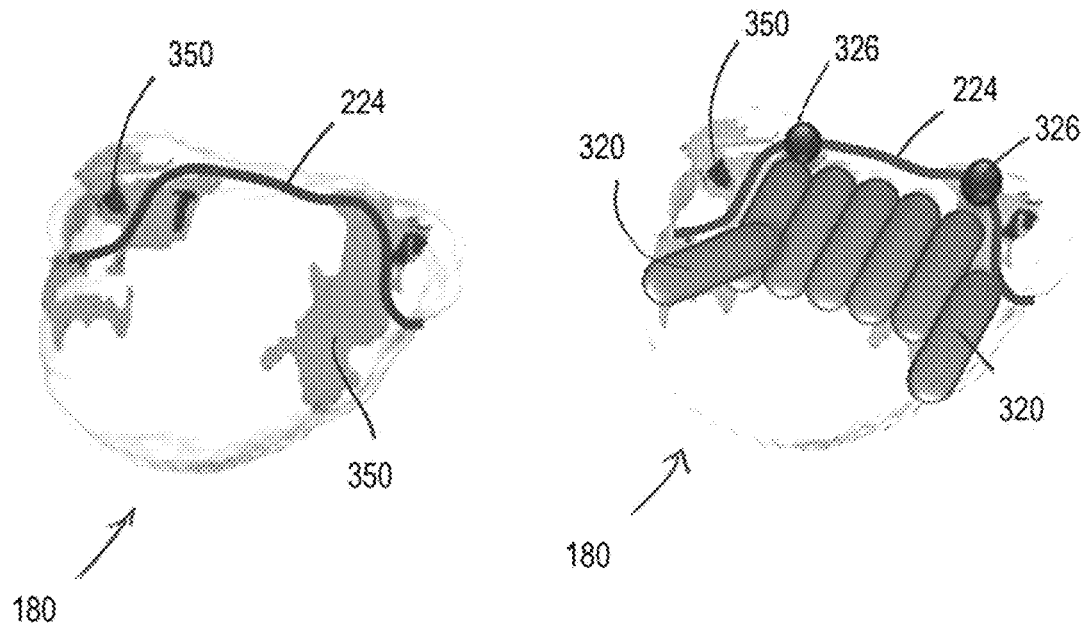
Figure 2C:
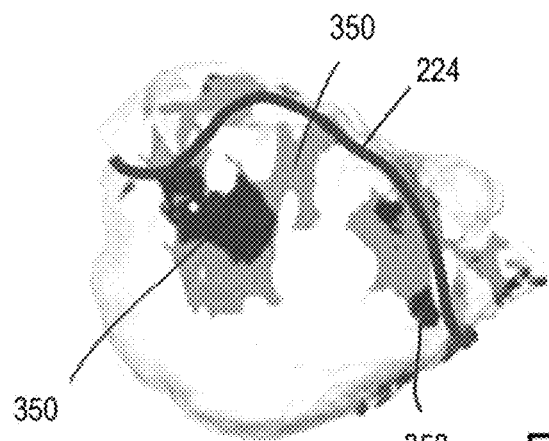
Figure 2C:
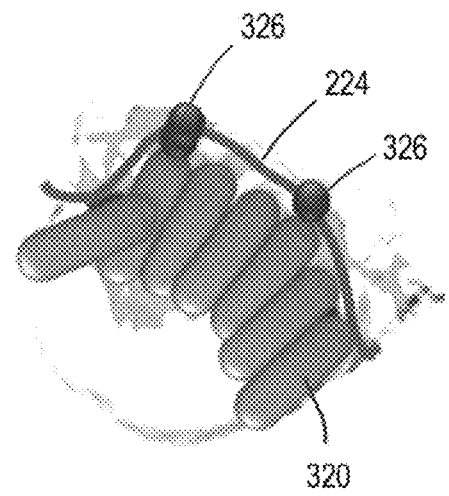
Figure 2D:
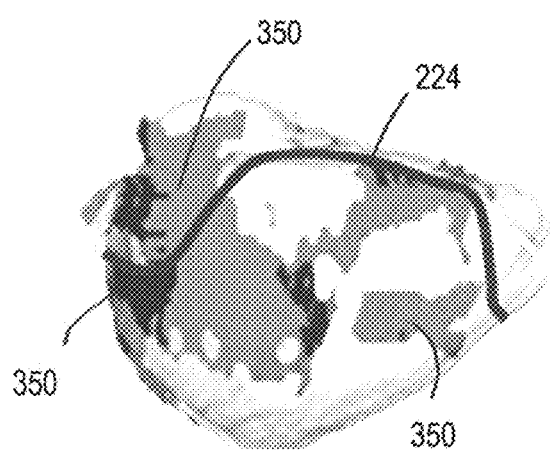
Figure 2D:
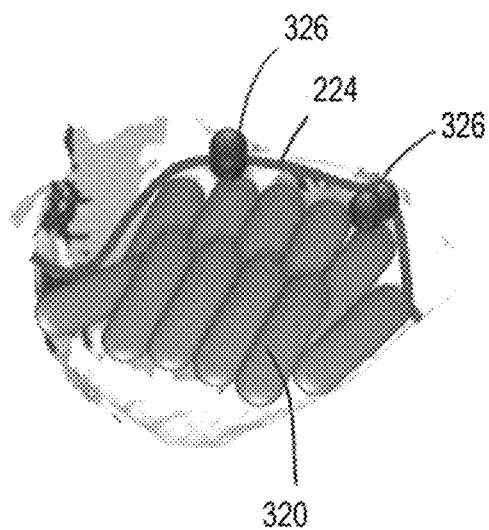

FIGS. 2A through 2C illustrate 3D images of hearts 180 taken by an MRI and 3D bi-polar voltage map of an EAM system. FIG. 2A an image of a heart classified as having areas of minimal fibrosis 350 identified. In response, a lesion pattern can be applied comprising epicardial lesions 320 and/or endocardial lesions 326. FIG. 2B shows an image of a heart 180 classified as having mild fibrosis 350 formation and the associated lesion pattern comprising epicardial lesions 320 and/or endocardial lesions 326. FIGS. 2C and 2D respectively illustrate hearts 180 having moderate (FIG. 2C) and severe (FIG. 2D) fibrosis and the accompanying patterns. It is understood that the treatment patterns are made in response to the stressed affected areas and additional patterns are considered to be within the scope of this disclosure.

Figure 3A:
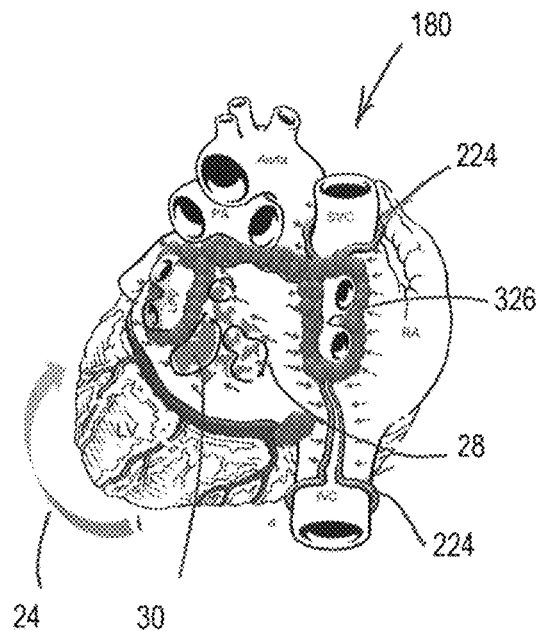
FIGS. 3A to 3D show various conventional treatment patterns that can be used in conjunction with atrial fibrillation treatments described herein.
Figure 3B:
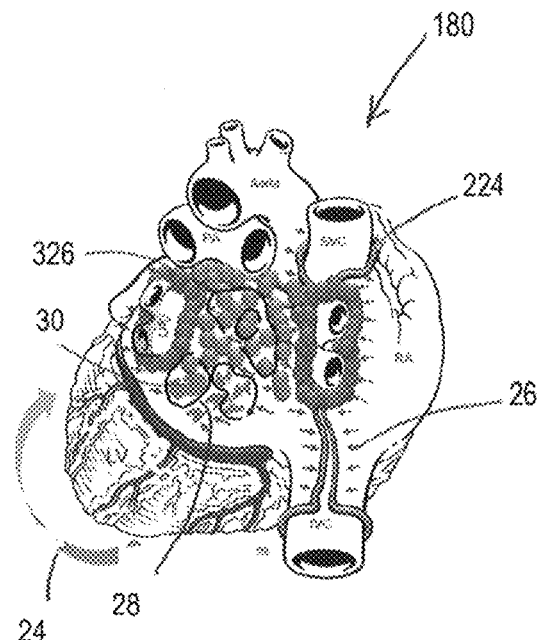
Figure 3C:
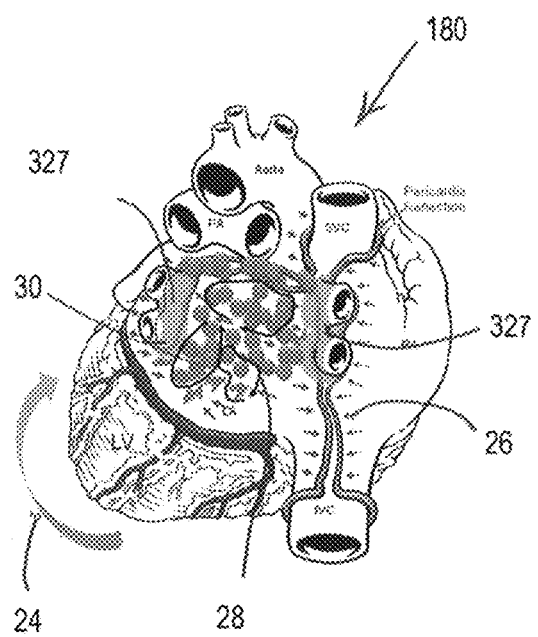
Figure 3D:
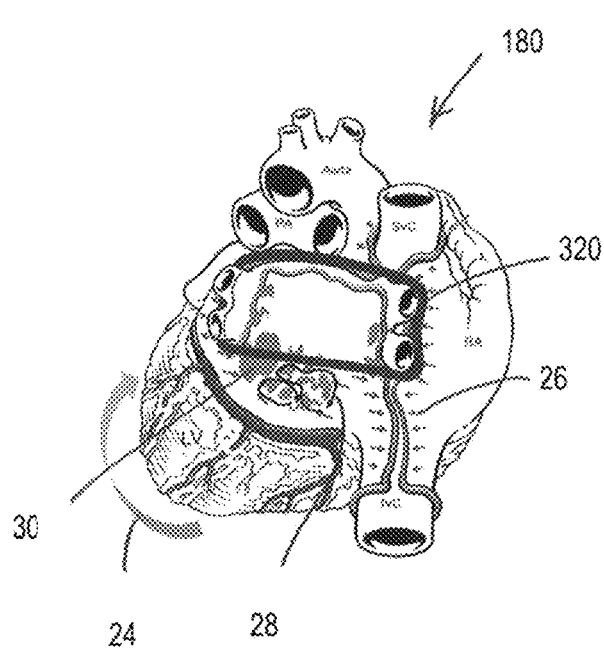

In addition, the treatment patterns disclosed herein can be used in conjunction with additional types of atrial fibrillation treatments. FIG. 3A is a schematic representation of a heart 180 with a number of point endocardial lesions formed around the pulmonary veins and the pericardial reflection 224 extending therebetween. FIG. 3A illustrates the potential areas of fibrosis 30 and corresponding arrhythmogenic wave fronts 28 responsible for atrial fibrillation. Continued displacement of the heart 28 can lead to continued atrial stretch of the left atrium that can prolong progressive remodeling of the atrial tissue. FIG. 3B illustrates additional endocardial point lesions 326 placed between the left and right pulmonary veins. Such lesions cannot completely ablate the posterior atrium or reduce stresses generated therein. Similarly, FIG. 3C illustrates cyroablative lesions 327 formed around the pulmonary veins but leaving areas of fibrosis that can continue to undergo atrial remodeling and stress in response to displacement 24 of the heart 180. FIG. 3D illustrates an epicardial "box" lesion 320, which may reduce fibrosis and arrhythmogenic wave fronts within the "box" lesion 320. However, areas of fibrosis 320 exterior to the "box" lesion 320 can still give rise to arrhythmogenic wave fronts 28. In each case, additional epicardial and/or endocardial treatment patterns can be supplemented to structurally support the atrial tissue and lessen the effects of the stress affected areas.

Figure 4B:
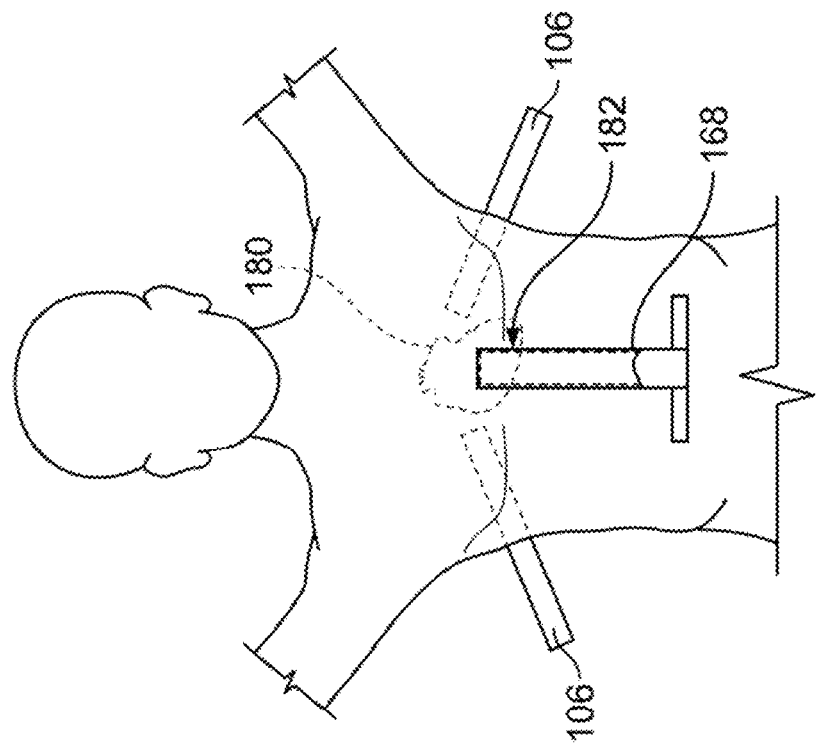
FIGS. 4A and 4B illustrate various approaches for inserting devices to access the heart for performing a bi-atrial lesion pattern.
Figure 4A:
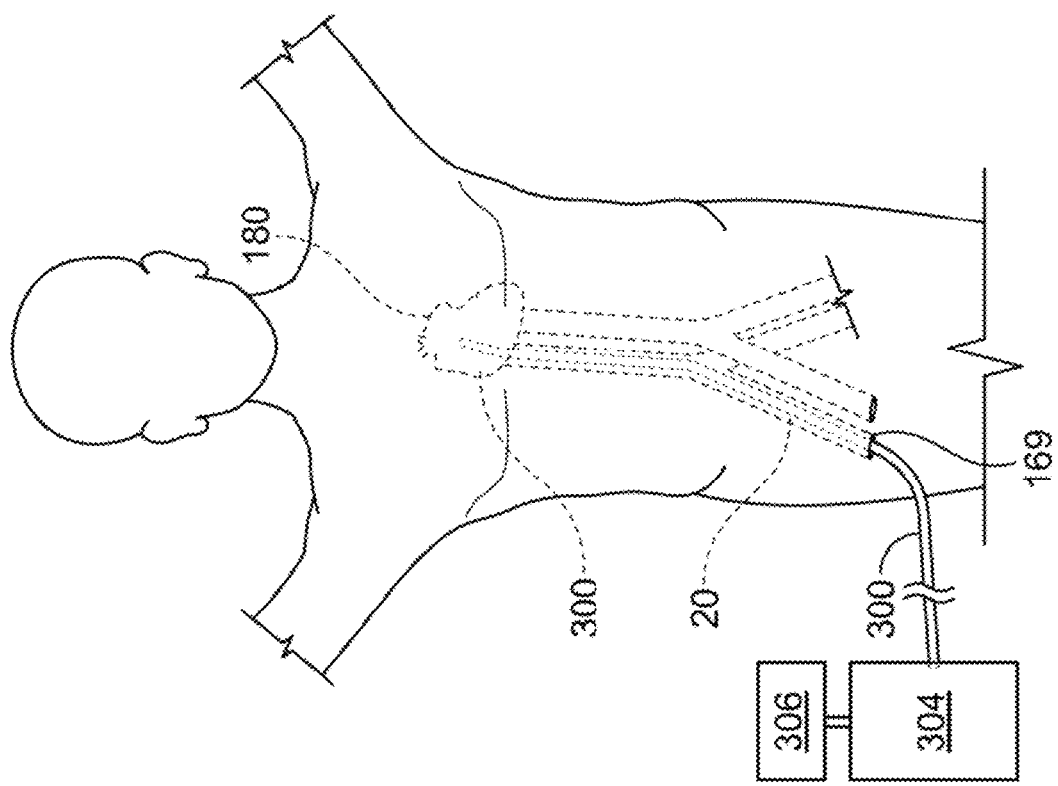
Figure 4C:
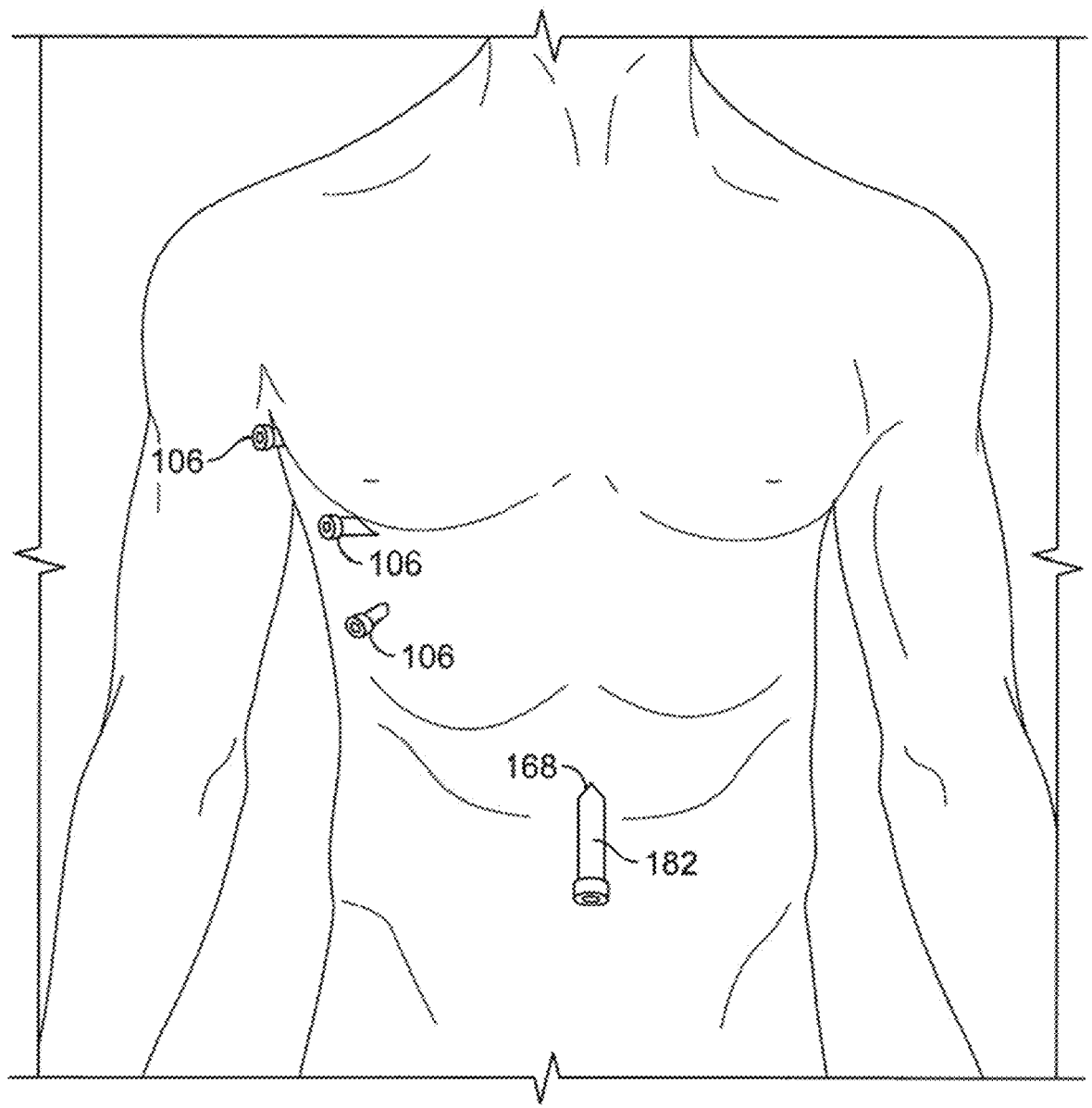
FIG. 4C shows a variation of insertion of an access device to achieve the diaphragm access technique described herein for use with a bi-atrial lesion pattern. In this variation, optional ports can be inserted to provide access to the right side of the thoracic cavity.

FIGS. 4A to 4C illustrate various approaches for inserting devices to access the heart for performing lesion pattern as described herein. FIG. 4A illustrates an example of inserting a device 300 device through an incision 169 in the leg and into a femoral vein 20. In this example, the physician advances the device 300 into a right atrium 195 of the heart 180 to access the endocardial surface for treatment. As will be described herein, the device 300 can comprise a coagulation device that is configured to allow location of the working end of the device, when placed within the heart, from an endocardial or exterior surface of the heart. In alternate variations, the sole function of the device 300 could be to allow for location of the working end of the device. For example, the device 300 could comprise a coagulation device configured to allow for location of the working end from an endocardial surface. In another variation, the device 300 could comprise a guide wire or catheter that can be advanced within the heart, located, and used to deliver a separate coagulation device once a suitable location is identified.

The access procedure shown in FIG. 4A is for exemplary purposes only. Any access procedure that places a coagulation device in proximity to an endocardial location can be employed when the present procedures and methods are used for a cardiac treatment.

FIG. 4A also illustrates the device 300 as being coupled to a power supply 304. The power supply can optionally include hardware or a power supply for determining the location of a working end of the device 300 within the heart from an exterior or endocardial surface as described below. Optionally, this hardware or power supply can be separately coupled via a separate power supply 306. In such a case, the hardware 306 can be applied to conventional devices that would otherwise not be suitable to create a bi-atrial lesion pattern.

FIGS. 4B and 4C show examples of placement of access devices 182 (also referred to as a separator or an elevator herein) as well as trocars 106 for accessing an epicardial surface of the heart 180. Again, the procedure can include a conventional thoracic approach using trocars 106 or ports placed directly into the thoracic cavity. In an additional variation of the methods described herein, thoracic access can be obtained via an abdominal approach. This approach allows for improved posterior access of organs within the thoracic cavity.

In one variation, an access technique includes advancing an access device through an abdominal incision to create an access path to a thoracic cavity. Once a patient is prepared, as shown in FIG. 4B, an access device 182 is inserted through, at least a first, an abdominal, incision 168. The device is then advanced through the diaphragm (not shown) and placed adjacent or between organs for creation of a temporary cavity. FIG. 4B illustrates one example, in this variation; the surgeon places the access 182 between heart and the spine such that the esophagus can be separated from the posterior surface of the heart. However, it is not necessary to access the thoracic cavity via a diaphragm based approach.

It is important to note that the convergent coagulation pattern disclosed herein can be made without the use of any incisions into the chest wall to access the thoracic cavity, any lung deflation, or any dissections of the pericardial reflections. Instead, a variation of the procedure includes access of the pericardial space via an abdominal approach as disclosed below. However, alternate variations of the procedure and methods described herein can be augmented with one or more additional thoracostomy incisions or punctures allowing for placement of trocars 106 into the thoracic cavity. The trocars 106 permit insertion of surgical tools or visualization devices. Accordingly, the access device 168 allows for direct visualization of the posterior surface of the organs during manipulation of the instruments inserted through the right and/or left thoracostomy access ports 106. Moreover, use of the additional thoracostomy access sites with the access device 168 may permit the surgeon to visualize the anterior surfaces of anatomic structures, during the procedure. Once tissue obscures the surgical site from the surgeon's view via the thoracostomy access ports 106, the access device 168 allows the surgeon to have a posterior view of the surgical site. In some variations, the access device 168 is used alone without the additional thoracostomy access ports 106.

Figure 5A:
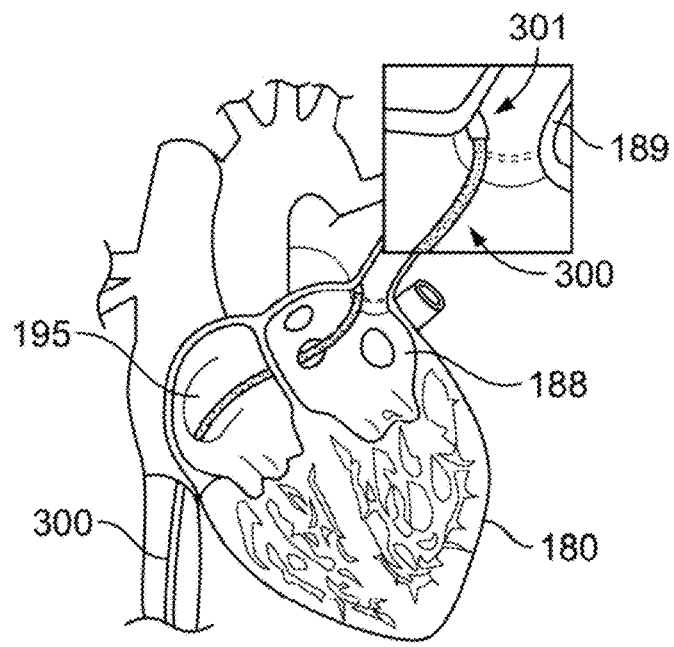
FIG. 5A illustrates an example of advancing the device into a heart for determining a location of the device from an exterior of the heart.

FIG. 5A illustrates an example of advancing the device 300 into a right atrium 195 across a septum and into the left atrium 188 to a pulmonary vein 189. In the illustrated variation, the device 300 comprises a visual light source at a working end 301. However, various other modalities can be employed to determine the location of the working end 301 from the exterior of the heart. As shown in FIG. 5A, a physician can advance the working end 301 of the device against or adjacent to tissue. A steerable sheath or device can be used to position the working end 301 where desired. Alternatively or in combination, the device 300 itself can have a steering mechanism or can be otherwise positionable.

Figure 5B:
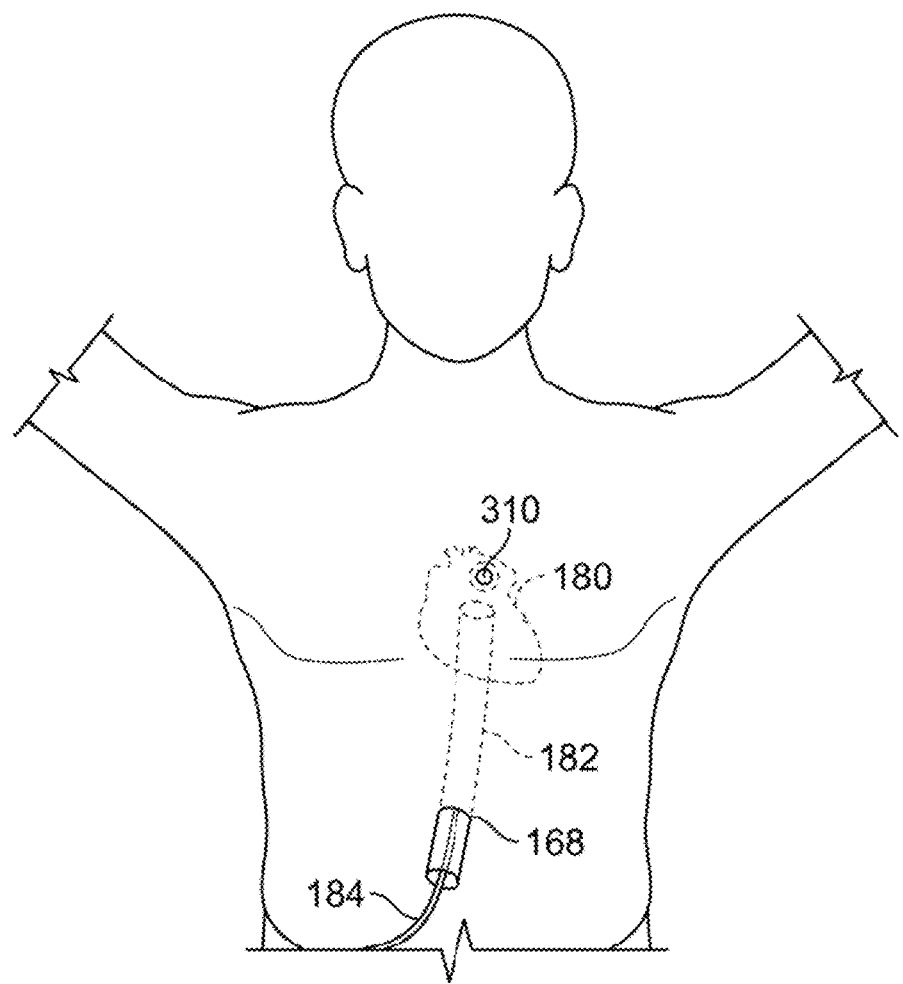
FIG. 5B represents an example of viewing the heart and observing an indicator of the position of the device within the heart where the observation occurs from the thoracic cavity and epicardial surface.

FIG. 5B represents an example of viewing the heart 180 from the thoracic cavity and epicardial surface. As shown, when the working end 301 of the device 300 is advanced against or near tissue on the interior atrial surface, the physician can observe an indication 310 from the epicardial surface. Here, the device 300 applies a locational energy to produce the indication 310. In one variation of the procedure, the physician observes the indication 310 using an access device 182 as described herein that is advanced through an abdominal incision, through the diaphragm and into the pericardial space. A scope 184 (either a separate scope or one that is integrated into the access device 182) allows the physician to visualize the indication 310. In this variation, the physician does not need to place additional access devices, ports, trocars or other similar means in the chest to access the pericardial space. Instead, the entire convergent coagulation pattern is performed via abdominal and vascular access.

In certain variations, this locational energy is contrasted from ablation or coagulation energy as the locational energy does not significantly affect the tissue. However, alternative variations of the method can include increasing the intensity or power of the locational energy to sufficiently create a coagulation or ablation lesion.

Although, FIG. 5A illustrates the working end 301 of the device 300 in a pulmonary vein, for sake of illustration, FIG. 5B shows the working end within the left atrium of the heart. Since the observation is real-time, the physician can reposition the working end 301 of the device 300 as desired. For example, the physician can reposition the working end 301 until the indication 310 shows that the position of the working end 301 on an endocardial surface is adjacent to an existing coagulation lesion on the epicardial surface.

Figure 6A:
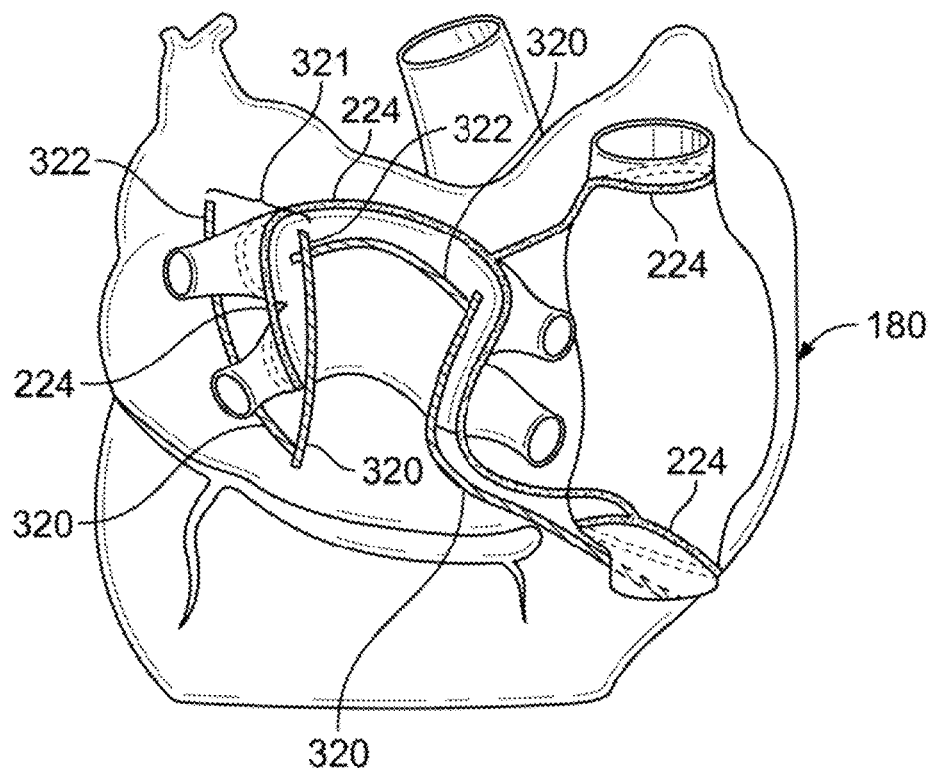
FIGS. 6A to 6E illustrate an example of creating a bi-atrial lesion pattern on a posterior surface of the heart.

FIGS. 6A to 6E illustrate an example of creating a bi-atrial lesion pattern on a posterior surface of the heart 180. FIG. 6A illustrates a posterior surface of the heart showing the various anatomic structures, including pericardial reflections 224 as well as the contoured surfaces and presence of the cardiac structures. These anatomic structures make the creation of a full coagulation pattern a difficult task. FIG. 6A shows partial coagulation pattern created on an epicardial surface of the heart 180. Various devices and methods to access the posterior surface and create the partial lesion pattern are discussed below. As shown, the partial coagulation pattern comprises a number of coagulation lesions 320 that intersect to provide an electrical barrier to prevent electrical impulses or wavelets from propagating in tissue and across the lesion. However, FIG. 6A also illustrates the condition where a gap 321 exists between ends 322 of a pair of lesions 320. In order to complete the coagulation pattern and fully electrically isolate tissue, the physician would be required to dissect pericardial reflections 224 along the epicardial surface and place a coagulation lesion across the gap. However, dissecting the pericardial reflections increases procedure time and causes increased risk during the procedure as discussed above.

Figure 6B:
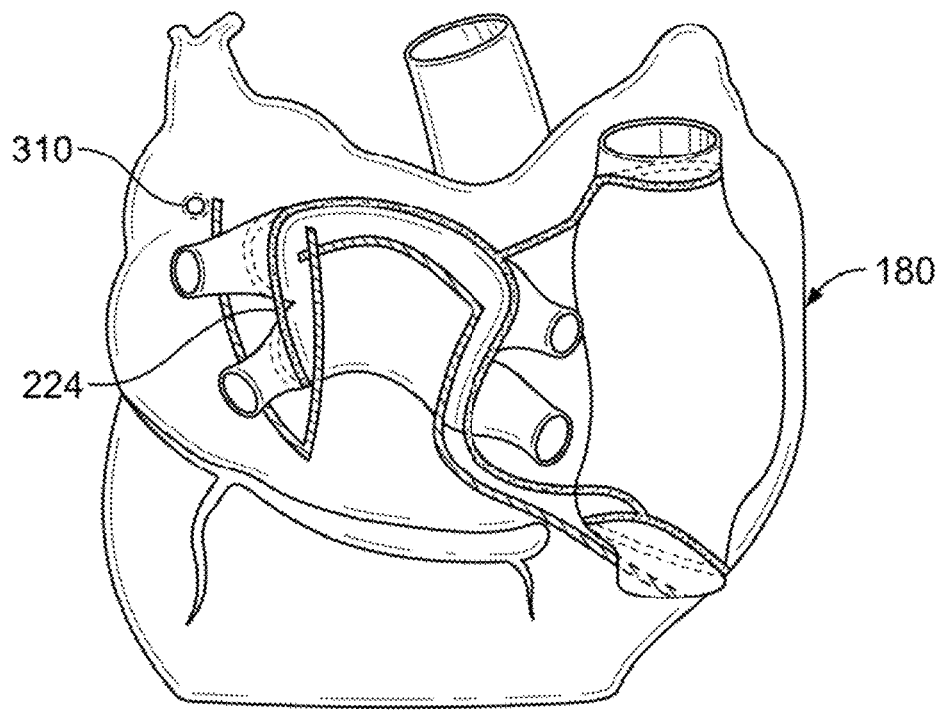

FIG. 6B illustrates the state where the physician advances a device into the chamber of the heart 180 via a vascular approach (similar to that shown in FIG. 5A). As discussed herein the device can comprise a sensor or other source of electromagnetic energy. The device is then advanced against or close to an endocardial surface within the heart. The sensor or source of energy is then actuated to allow a physician to observe the location of the device through the tissue. In the example shown, the physician observes the epicardial surface for an indicator 310 that represents the location of the device within the heart. Once the physician is satisfied that the location of the internal device is positioned to sufficiently form an endocardial coagulation lesion that would overlap, intersect, cross, or otherwise join to one of the epicardial lesions 320, the physician can begin to make an endocardial lesion across the gap section 321 and close or complete the ablation pattern. In this manner, the endocardial lesion and the epicardial lesion form a contiguous lesion that prevents an electrical impulse from propagating in the tissue through the pattern defined by the contiguous lesion.

Figure 6C:
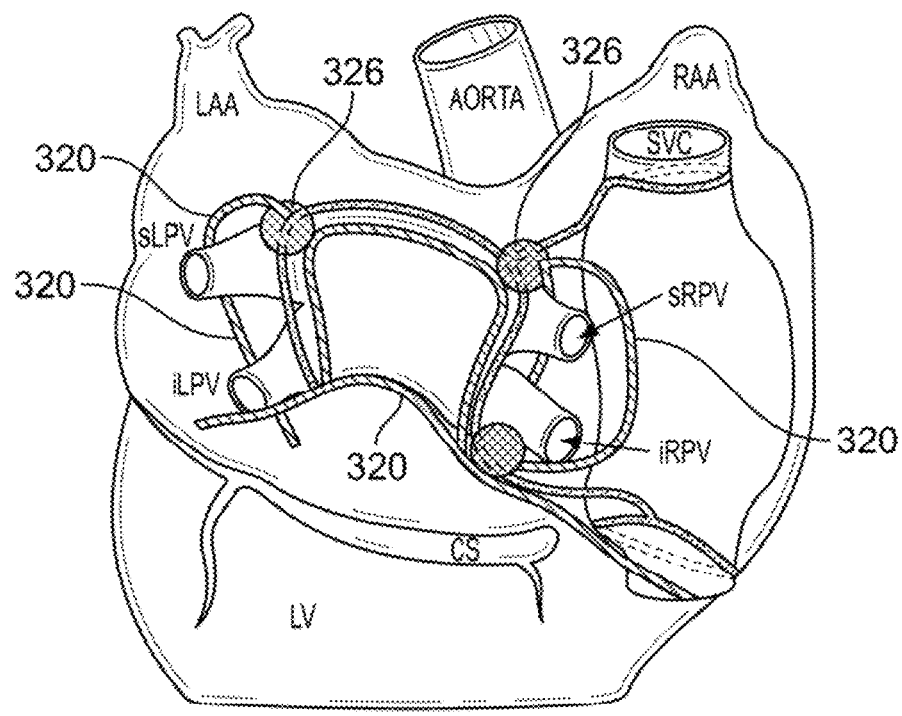

FIG. 6C shows one variation of a complete convergent coagulation pattern as the endocardial lesions 326 are created on the inner atrial surface. These lesions 326 intersect, join, and/or overlap epicardial lesions 320 to form the completed bi-atrial coagulation pattern. These endocardial lesions 326 are formed in areas on an endocardial surface that eliminate the need for dissecting pericardial reflections which attach the pericardium to the epicardial surface.

As discussed above, this technique allows creation of the desired coagulation pattern without dissection of any pericardial reflections. Instead, as shown in FIG. 6C, the epicardial coagulation occurring on the inner atrial surface creates lesions around the pericardial reflections since the lesions are on the inner surface of the heart. In addition, variations employing an abdominal entry approach for creating the epicardial lesions, allow a physician to create epicardial lesions without creating openings in the chest and without deflating the lungs. The abdominal entry access method also allows increased visualization around the areas of the pericardial reflections so rather than dissecting the reflections, a physician can use an epicardial coagulation device (or other device) to gently distort or push against the pericardial reflection to minimize the gap between lesion patterns.

In one variation of the method, the coagulation device placed on the outer surface of tissue can comprise one pole of an RF energy system where the second pole of that RF energy system is located on a second device that is on the inner surface of the tissue. Accordingly, during application of energy current flows between the two devices and through tissue to create a lesion. Another benefit of such a system is that the devices can be used to measure impedance of the tissue between the devices. In general, the impedance will increase as the devices are moved farther away and will decrease when the devices are closer together but on opposite sides of the tissue.

Figure 6D:
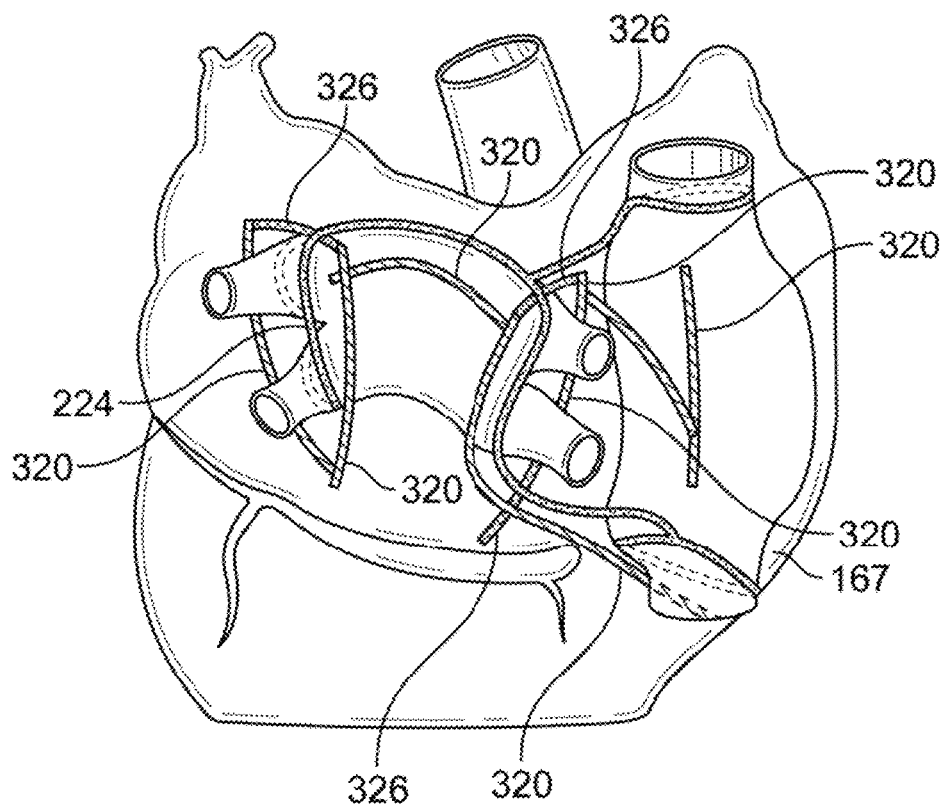

FIG. 6D illustrates another variation of a bi-atrial coagulation pattern. In this variation, an epicardial coagulation device creates epicardial lesions 320 around pericardial reflections 224 as shown. As with the previous technique, this procedure allows for creation of epicardial lesions 320 without dissection through the pericardial reflections. A commercially available ablation device is then used to create endocardial lesions 326 to connect gaps in the areas caused by the pericardial reflections on the epicardial surface.

Figure 6E:
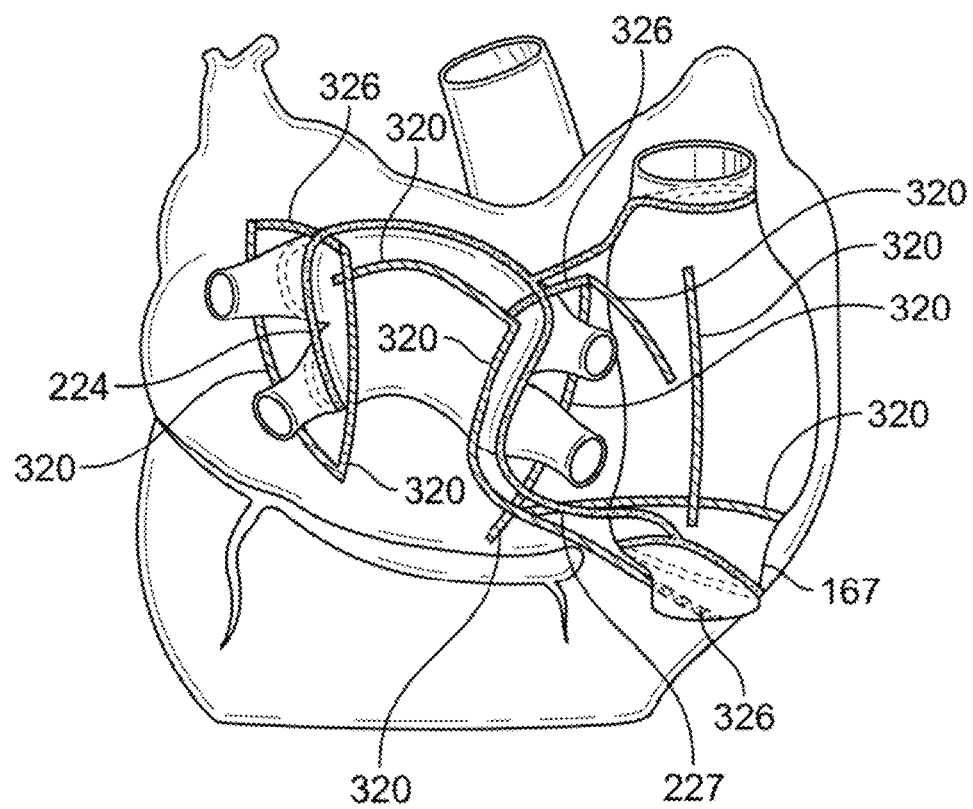

FIG. 6E illustrates another variation of a bi-atrial coagulation pattern. In this technique, an epicardial coagulation device creates epicardial lesions 320 around the pericardial reflections 224 as shown. However, the reflection located in front of the oblique sinus, as shown at 227, is dissected as well as the oblique sinus. Dissection at these locations is relatively easy because the location is in line with an access port when using a trans abdominal approach as disclosed below. Once the oblique sinus has been accessed, the right atrium lesions can be completed. Once again, an endocardial coagulation device creates endocardial lesions 326 across gaps that are at the top of the pulmonary veins. The endocardial coagulation device can also extend the endocardial lesion in front of the inferior vena cava.

The advantages of a bi-atrial technique versus a totally endocardial technique is that a bi-atrial pattern allows for a full lesion pattern, including left-atrium to right-atrium lesions where such lesions are only accessible from an epicardium. Moreover, the bi-atrial pattern allows the potential to coagulate the Ganglionated Plexi, which is only accessible from the epicardium. As noted above, the use of epicardial lesions minimizes the risk of coagulating from the endocardium outward. Also, the technique allows for preservation of atrial function since coagulation lines are along the pericardial reflections that tether the atrium and are relatively immobile.

The advantages of a convergent, combined epicardial and endocardial technique over an epicardial only techniques include: the ability to create a flutter lesion at the tricuspid isthmus, the ability to create lesions that connect the epicardial linear segments at the pericardial reflections to avoid the need to dissect the reflections resulting in decreased procedure time, and assuring lesion integrity and pulmonary vein isolation via endocardial mapping.

Figure 7A:
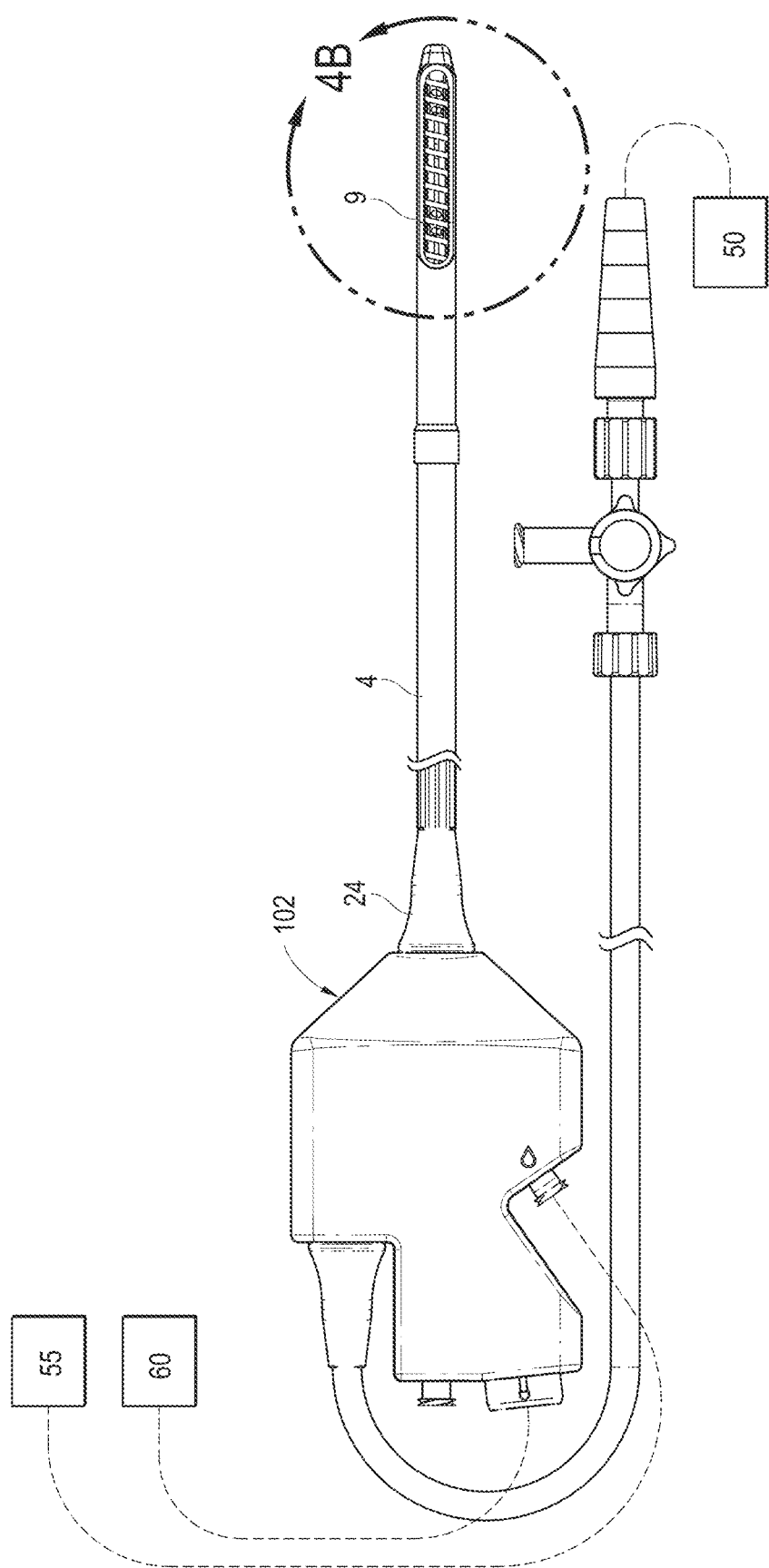
FIGS. 7A to 7C illustrate a variation of a coagulation probe configured with pacing and/or sensing capabilities as well as a coagulation element within a single probe.

FIG. 7A illustrates A variation of a coagulation device for use with the present methods. In this example the device consists of a probe 2 and a handle 102. In this variation, the probe 2 again includes a shaft 4 having a housing 9 at a distal section of the shaft 4. However, the variation of FIG. 7A shows a variation of a coagulation probe 2 having the capability of pacing and/or sensing as well as an element coupled to a single probe. As described above, variations of the coagulation device can employ any variety of shapes and sizes for the handles and/or housing. In the example shown, the handle 102 includes a plurality of connectors for connecting the probe to a power supply 60, a fluid source 55 and a vacuum source 50. The device can also include a strain relief 24 as well as any other features to accommodate flexibility of the shaft.

Figure 7B:
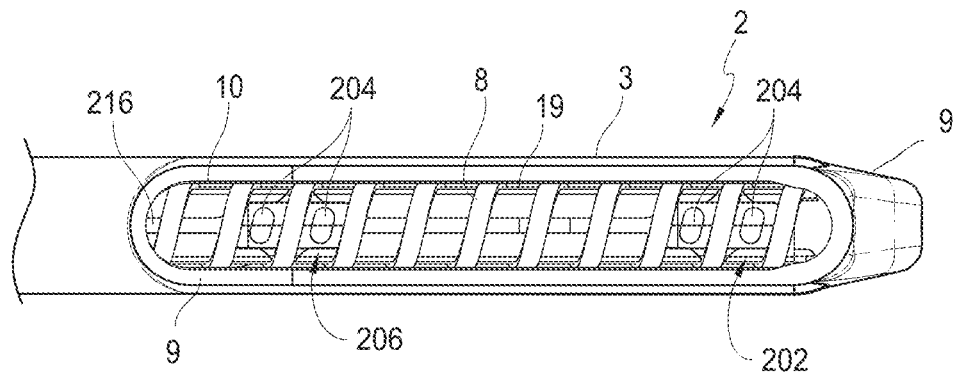

FIG. 7B illustrates a magnified view of the distal end of the probe 2 of FIG. 7A. In this variation, the probe 2 includes a housing 3 having both an energy transfer element 8 and a plurality of diagnostic element assemblies 202 and 206 exposed at the opening 10 of the housing 3. The illustrated variation shows a probe 2 having a coiled energy transfer element 8 with two diagnostic element assemblies 202 and 206. However, additional variations of probes can include a non-helical energy transfer element 8 with any number of diagnostic element assemblies or even a single assembly. As shown, electrodes 204 on the diagnostic element assemblies 202, 206 are positioned between the electrode or element surface (in this case the turns of the coil.) As described herein, the areas between the turns of the coil permit a vacuum force within the housing to secure the opening against tissue and draw the tissue into opening so that tissue contacts the energy transfer element 8 as well as the diagnostic electrodes 204. The housing 3 can also include a flexible lip 9 or extension that assists in securing tissue against the opening 10 to form a vacuum. In some variations of the device it important that the electrodes 204 on the diagnostic assemblies remain electrically isolated from the energy transfer element 8. This can be accomplished by positioning the diagnostic electrodes 204 within the spacing of the element 8 as well as electrically insulating the interior of the element 8. As shown below, the probe 3 can include one or more liners 19 that can support the helical element 8 and/or provide additional insulation to electrically isolate the diagnostic electrodes 204.

Figure 7C:
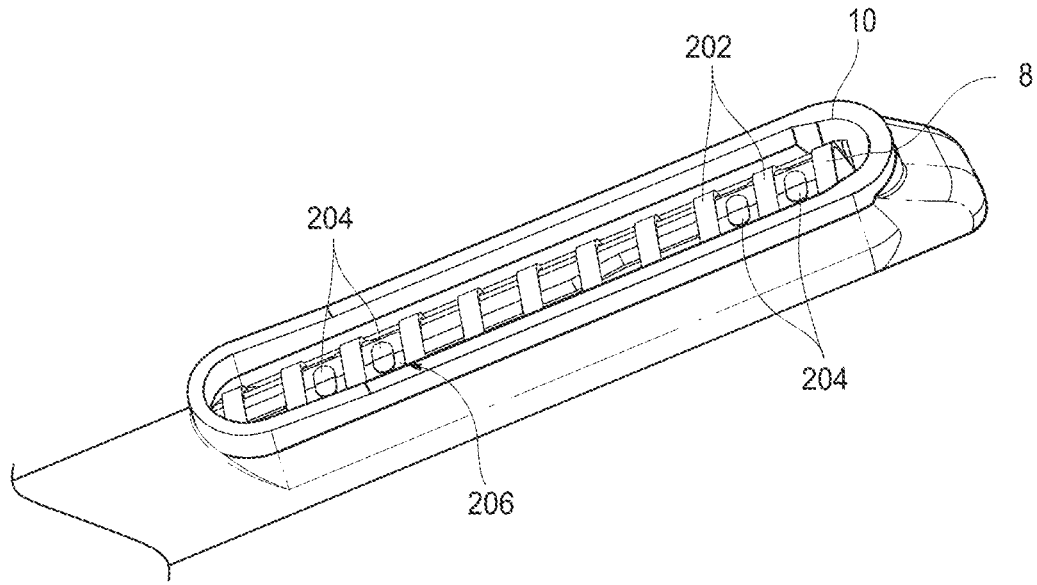

FIG. 7C shows a perspective view of the energy transfer element 8 located within an opening 10 of the probe 2. As shown, the energy transfer element 8 and diagnostic element assemblies 202 and 206 are recessed within the opening 10 so that when the lip 10 forms a seal against tissue the tissue is drawn into the opening 10 and engages the element 8 and electrodes 204 of the diagnostic assemblies 202 and 206.

Figure 8A:
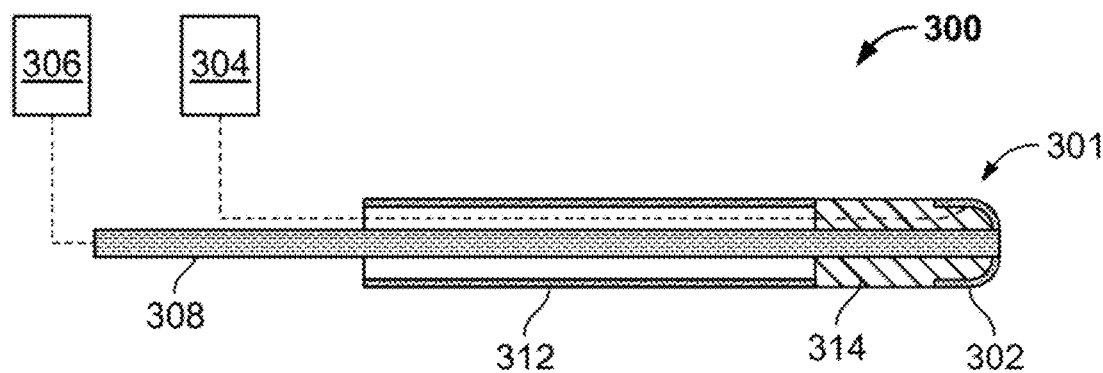
FIGS. 8A to 8C demonstrate various examples of devices for advancement into the heart.
Figure 8B:
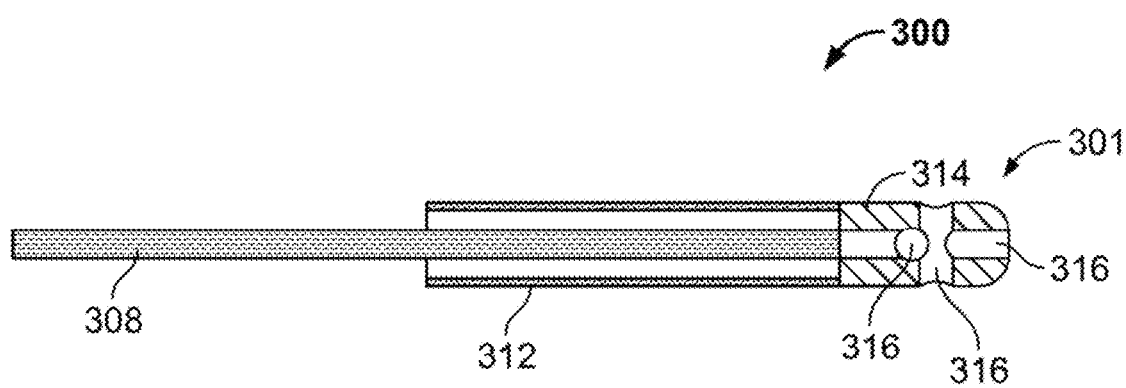
Figure 8C:
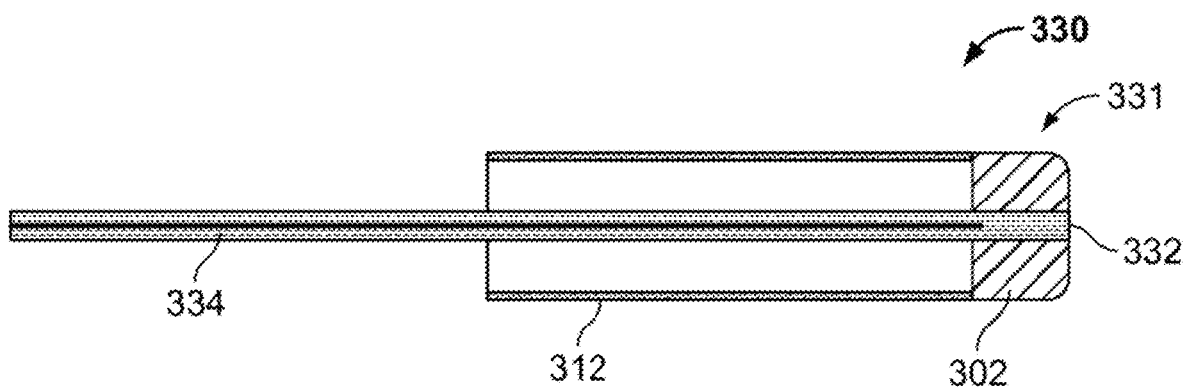

As discussed above, certain variations of the methods for creating atrial lesion patterns employ devices that permit location of the device through tissue. FIGS. 8A to 8C illustrate some exemplary devices that assist the physician in locating the coagulation device through tissue where the device includes a source of electromagnetic energy at a working end.

FIG. 8A illustrates a device where the source of electromagnetic energy comprises an illumination source. Accordingly, an illumination power supply 306 can be coupled to an illumination source 308 (such as an optical fiber) that extends through the body 312 of the device 300 and is exposed at or near a working end 301 of the device 300. In some variations, the illumination source 308 can comprise a light or light emitting diode positioned at the working end 301. Such a configuration could employ an external power supply or the power supply can be self-contained in the body 312 of the device 300. The illumination source 308 can optionally terminate in an illumination tip 314 that is configured to disperse the light or other energy about the circumference and front end of the working end 301. For example, the illumination tip 314 can comprise a transparent or translucent material such that the energy passes from the illumination source 308 into the illumination tip 314. In another variation, the illumination tip 314 can comprise a transparent or translucent balloon member. In yet another variation, the device 300 can comprise an intravascular catheter that is equipped with one or more electrodes 302 located at or near the working end 301 and coupled to a power supply 304. In such a case, the device 300 can comprise a traditional coagulation catheter with an illumination source coupled thereto or one in which the illumination source is constructed as part of the device.

FIG. 8B shows another variation of a device with an illumination source 308 coupled to an illumination tip 314. As noted above, the working end 301 may or may not have an electrode coupled thereto. In any case, the illustrated variation includes an illumination tip 314 having one or more openings or channels 316 for directing energy from the illumination source 308 in a desired pattern about the tip 314.

FIG. 8C illustrates another variation of a device 330 for creating lesion patterns. In this variation, the device 330 comprises an endocardial coagulation device 330 having one or more electrodes 302 located at a working end 331. The device 330 further includes one or more temperature detecting elements 332. As discussed below, as an endocardial catheter creates lesions, the temperature of the cardiac tissue rises. This change in temperature can be sensed with the temperature detecting element 332. The temperature detecting element can be of several different types known and used for measuring temperature of tissue or other temperature measurements. For example, the temperature detecting element can be a thermocouple an infrared temperature detecting device. Furthermore, the temperature detecting element can be a non-contact detecting element, such as an IR thermometer that is coupled to one or more of the access devices described below.

Clearly, any other temperature detecting device is within the scope of this disclosure. As an epicardial device coagulates tissue on an epicardial surface, the physician places the device 330 in contact with endocardial cardiac tissue to detect for a rise in temperature. As the temperature rises indicating that the device is properly placed adjacent to an epicardial lesion, the device 330 can be positioned so that the electrode 302 is energized to create an endocardial lesion at the site on the endocardial surface. In the illustrated example, the temperature-detecting element 332 can be coupled to a power supply (not shown) via the same conducting members 334 that couple the electrode 302 to a source of coagulation energy.

The source of electromagnetic energy described herein can comprise any form of electromagnetic energy that can be detected through tissue. Some examples of such energy include visible light, coherent light (e.g., a laser), ultraviolet light, magnetic energy, electrical energy, etc. Although the previous examples show the use of a visible light or laser, additional variations include electromagnetic energy that is not visible. Furthermore, as shown below, the electromagnetic energy source can communicate with a sensor that is placed on the opposite side of the tissue wall where the sensor is configured to measure the electromagnetic energy to determine the proximity between devices.

Figure 9A:
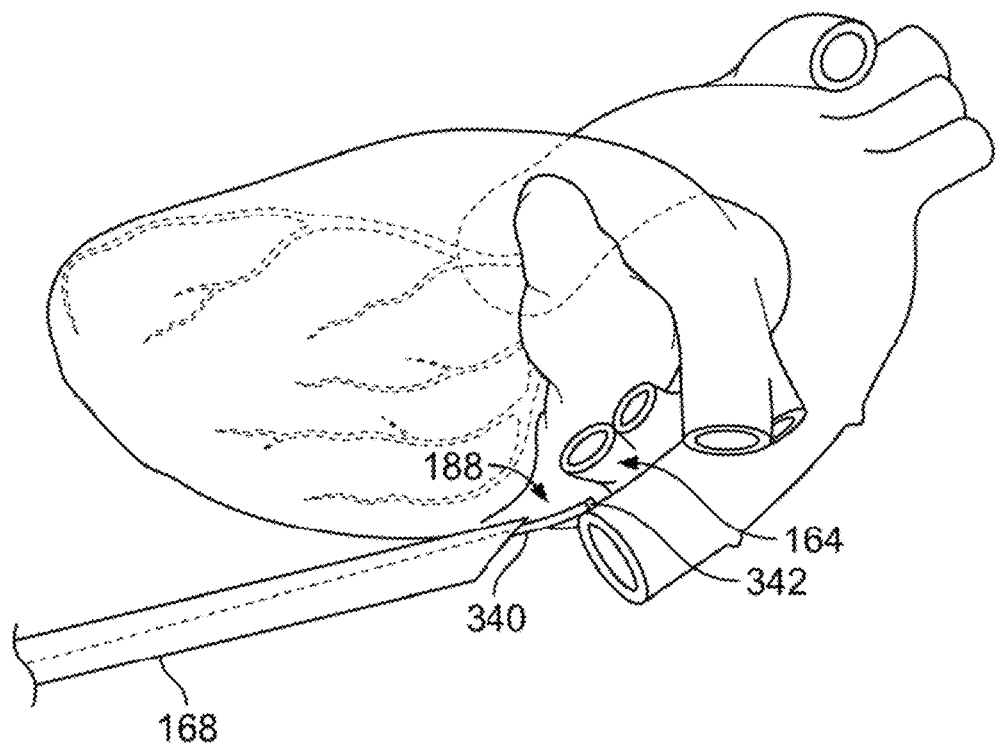
FIG. 9A shows an example of an access device providing a pathway to a posterior atrial surface with a sensor advanced through the access device.

For example, FIG. 9A illustrates an example of an access device 168 providing a pathway to a posterior atrial surface 188. The physician then advances a device 340 having a sensor 342 for detecting one or more paired sensors (or other sources of electromagnetic energy) on the opposite side of the atrial wall. The sensor 342 can be configured on a stand alone device or it can be incorporated into the epicardial coagulation devices as discussed herein.

Figure 9B:
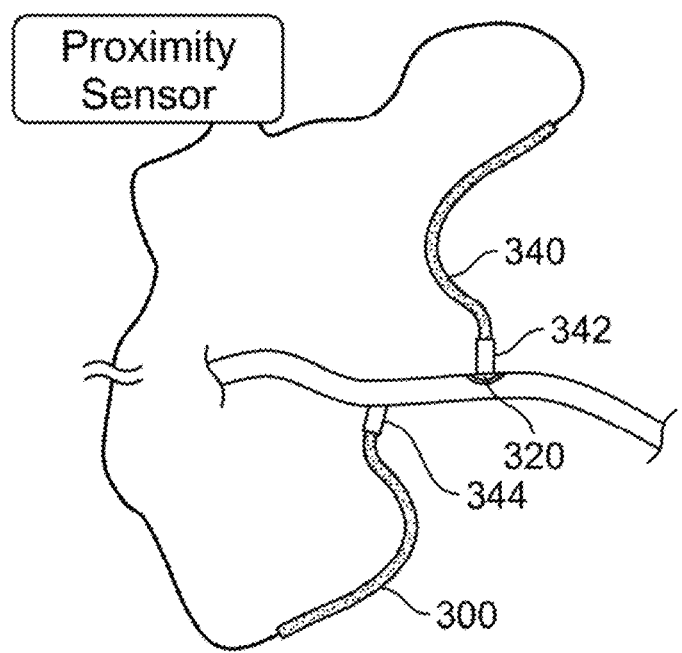
FIG. 9B provides a partial cross sectional view of the device of FIGS. 8A-8C as it is placed against tissue to locate a second sensor device within the heart.

FIG. 9B provides a partial cross sectional view of the device 340 of FIG. 9A as it is placed against tissue to locate a second sensor device 300. In practice, the physician can position the sensor 342 on or near the epicardial lesion 320. Then, the second sensor device 300 is moved on the opposing side of the tissue wall to detect the proximity of the catheter on the endocardial surface through non-visual means. By ensuring that the proximity of the two devices 300, 340 falls within a certain distance, the physician can increase the probability that lesions formed on each surface will connect to form the contiguous lesion. In some variation, the proximity sensor 342 and/or 344 can be calibrated such that the system will only alert to the proximity of the two devices when they are close enough to cause a connecting lesion. In one example, a physician can place the epicardial device 340 on the most distal portion of the epicardial lesion set. Then, the physician moves the endocardial device 300 to create the endocardial lesion. When the proximity sensor alarm is activated, the physician can be sure that the two lesions are connected Various technologies can be used to detect the proximity of the two devices. One method involves detecting the impedance between the epicardial and endocardial devices. Using this method, both devices are part of the same AC circuit and the impedance of the circuit can be measured. As the devices are moved toward each other, the impedance will drop. Once a pre-set threshold is reached (one that ensures a connecting lesion) an alarm sounds alerting the physician that the two devices will create a connecting lesion.

Another method of detecting proximity utilizes a magnetic detector. The epicardial device contains a micro magnetic field generator and detector. The endocardial catheter contains a ferrous element. When the ferrous element enters the magnetic field of the epicardial device, the magnetic field is disturbed and is detected by the epicardial device. The detector would be calibrated such that the system will only alert to the proximity of the two devices when they are close enough to cause a connecting lesion.

Another variation to create matching lesions for a coagulation pattern involves the use of an access device with a modified light source. The access device is inserted into a pericardial space to visualize lesions created from inside the heart. Several technologies are available that utilize specific wavelengths of light to enhance the visualization of tissue structures.

One such technology uses blue and green light to penetrate superficial tissue surfaces and visualize changes in the tissue (such as detecting the presence of blood vessels). Irradiating the tissue with these or other wavelengths of light can detect the presence or absence of ablated/coagulated tissue. The healthy tissue shows up as a different color from the damaged, ablated tissue. These imaging devices using narrow band imaging (provided by Olympus) can be combined with the access devices described herein to create joining lesions.

Another technology provided by Novadaq Technologies uses blue light to excite the naturally occurring flourophors in healthy tissue. Cells contain molecules, which become fluorescent when excited by ultraviolet or near ultraviolet/visible radiation of suitable wavelength. This occurrence is known as autoflorescence. When tissue is damaged, it exhibits reduced autoflorescence. By utilizing this phenomenon, tissue that has been ablated can be distinguished from healthy tissue.

Another similar technology utilizes a narrow band of light (such as a laser) to excite a fluorescing non-toxic dye such as indocyanine green (ICG). The use of a dye allows the detection of a lesion because the ablated tissue will have little to no perfusion of blood through it. Therefore the dye will not appear within the boundaries of the lesion, but will appear is all other tissue. The tissue surrounding tissue will fluoresce while the lesion itself will not.

As discussed above, creation of a lesion can be performed with any conventional access to the thoracic cavity. Furthermore, the methods and devices described herein may be used in conjunction with, or as an alternative to the conventional approaches described herein.

The methods and techniques described herein to treat atrial tissue can employ any traditional coagulation device for either the epicardial coagulation patterns or the endocardial coagulation patterns. The energy modalities can include those commonly used modalities, such as, but not limited to RF energy, a laser energy, infrared heating, chemical ablation, cryogenic ablation, microwave energy, and resistive heating. Examples of improved coagulation devices for creating lesions are disclosed in: U.S. Pat. No. 6,893,442 filed on Jun. 14, 2002 issued on May 17, 2005; U.S. Pat. No. 7,063,698 filed on Apr. 29, 2003 issued on Jun. 20, 2006; U.S. Pat. No. 7,410,487 filed on Mar. 30, 2005 issued on Aug. 12, 2008; U.S. Pat. No. 7,572,257 filed on Aug. 18, 2005 issued on Aug. 11, 2009; U.S. Patent Publication No.: US 2006-0200124 A1 filed on May 23, 2006; US 2006-0206113 A1 filed on May 12, 2006; US 2006-0235381 A1 filed on May 12, 2006; US 2007-0043351 A1 filed on Apr. 21, 2006; US-2007-0250058-A1 filed on Apr. 19, 2007; US-2008-0114354-A1 filed on Nov. 9, 2006; US-2008-0114355-A1 filed on Nov. 9, 2006; US-2008-0243119-A1 filed on Jun. 6, 2008; and US-2009-0254009-A1 filed on Jun. 16, 2009. The entirety of each of which is incorporated by reference herein.

Methods allowing for access to the posterior surface of the heart can improve a physician's ability to observe the atrial surface. Such a technique, though optional, can assist the physician in creating a lesions. Examples of methods and devices for creating such access paths into the body are disclosed in U.S. Patent Publication Nos.: US-2007-0083082-A1 filed on Apr. 21, 2006; US-2008-0114342-A1 filed on Nov. 9, 2006; US-2008-0114288-A1 filed on Nov. 9, 2006; US-2007-0083225-A1 filed on Apr. 21, 2006; US-2007-0249991-A1 filed on Apr. 19, 2007; US-2009-0312783-A1 filed on Jul. 16, 2008; and US-2009-0270676-A1 filed on Apr. 23, 2008. The entirety of each of which is incorporated by reference herein.

FIG. 10A shows an example of placement of access devices 182 (also referred to as a separator or an elevator herein) useful for accessing a posterior surface of the heart. An access device 182 is inserted through, at least a first, an abdominal, incision 168. The device is then advanced through the diaphragm 170 and pericardium (not shown) and placed adjacent or between organs for creation of a temporary cavity. The procedure may include the use of one or more optional ports 106. The ports 106 in this variation are placed to allow access to the right side of the thoracic cavity. When placing right side access ports, the ports may be placed along any region of the body to provide access to the right side of the thoracic cavity.

When used, the ports 106 provide a surgeon with a second location to manipulate devices within the thoracic cavity. The access device 182 allows for manipulation/visualization of such devices in a posterior region of the thoracic cavity while the ports 106 allow for manipulation/visualization in the anterior region of the thoracic cavity. One such benefit of having dual access is that a guide wire or catheter can be inserted via the access device 182 and then navigated through and around organs towards the anterior region of the organ. In one example, use of this dual access allows for creation of a variety of coagulation regions on the pericardial tissue. Accordingly, the surgeon can dissect less (or no) pulmonary vein reflections and is able to directly visualize and control posterior left atrial lesions without creating left sided ports or incisions. The benefits of eliminating the left sided ports include decreased trauma to the patient and increased recovery time since the surgeon can allow the left lung to remain inflated.

What is claimed is:

1. A method for reducing and preventing atrial fibrillation in an atrial tissue of a heart, the method comprising:
   identifying an affected region of the atrial tissue, where the affected region of the atrial tissue is subject to a mechanical stress, where the mechanical stress is defined by one or more pericardial reflections and is produced as a result of an existing medical condition; and
   producing a treated section of the atrial tissue by applying energy thereto, where the treated section is located around the one or more pericardial reflections such that the treated section of the atrial tissue provides increased mechanical support to the affected region of the atrial tissue, where the increased mechanical support reduces the mechanical stress in the affected region of tissue to reduce an occurrence of atrial fibrillation within the atrial tissue, where the treated section of the atrial tissue and the affected region of the atrial tissue are located on different locations of the heart.

2. The method of claim 1, wherein the existing medical condition comprises a condition selected from the group consisting of obesity, hypertension, and cardiomyopathy.

3. The method of claim 1, wherein producing a treated section of the atrial tissue comprises producing a treated section of a left atrium.

4. The method of claim 1, wherein producing a treated section of the atrial tissue comprises producing a plurality of parallel and adjacent lesions on a posterior left atrium surface.

5. The method of claim 1, wherein producing a treated section of the atrial tissue comprises producing a plurality of adjacent and overlapping lesions on a posterior left atrium surface.

6. The method of claim 1, wherein producing a treated section of the atrial tissue comprises producing a plurality of lesions on an oblique sinus region of an atrium.

7. The method of claim 6, wherein producing the plurality of lesions on the oblique sinus region of the atrium comprises overlapping a plurality of the lesions to electrically silence the oblique sinus region.

8. The method of claim 1, where producing the treated section comprises ablating the treated section sufficiently to ablate at least one existing substrates of tissue causing atrial fibrillation.

9. The method of claim 1, wherein producing the treated section of the atrial tissue comprises producing at least a first treated section on an epicardial surface.

10. The method of claim 9, further comprising producing at least a second treated section on an endocardial surface.

11. A method for reducing and preventing atrial fibrillation in an atrial tissue of a heart, the method comprising:
    identifying an affected region of the atrial tissue, where the affected region of the atrial tissue is subject to a mechanical stress produced as a result of an existing medical condition; and
    producing a treated section of the atrial tissue by producing a plurality of adjacent and overlapping lesions on a posterior left atrium surface by applying energy such that the treated section of the atrial tissue provides increased mechanical support to the affected region of the atrial tissue, where the increased mechanical support reduces the mechanical stress in the affected region of tissue to reduce an occurrence of atrial fibrillation within the atrial tissue, where the treated section of the atrial tissue and the affected region of the atrial tissue are located on different locations of the heart.

12. The method of claim 11, wherein the existing medical condition comprises a condition selected from the group consisting of obesity, hypertension, and cardiomyopathy.

13. A method for reducing and preventing atrial fibrillation in an atrial tissue of a heart, the method comprising:

identifying an affected region of the atrial tissue, where the affected region of the atrial tissue is subject to a mechanical stress produced as a result of an existing medical condition; and producing a treated section of the atrial tissue to an epicardial surface by applying energy such that the treated section of the atrial tissue provides increased mechanical support to the affected region of the atrial tissue, where the increased mechanical support reduces the mechanical stress in the affected region of tissue to reduce an occurrence of atrial fibrillation within the atrial tissue, where the treated section of the atrial tissue and the affected region of the atrial tissue are located on different locations of the heart.

14. The method of claim 13, wherein the existing medical condition comprises a condition selected from the group consisting of obesity, hypertension, and cardiomyopathy.

* * * * *